(12) United States Patent
Hou et al.

(10) Patent No.: US 12,397,132 B2
(45) Date of Patent: Aug. 26, 2025

(54) RADIOPAQUE MARKER AND DELIVERY SYSTEM

(71) Applicant: BOSTON SCIENTIFIC SCIMED, INC., Maple Grove, MN (US)

(72) Inventors: Dongming Hou, Plymouth, MN (US); Hongxia Zeng, Maple Grove, MN (US); Tim O'Connor, Galway (IE); Bryan Allen Clark, Forest Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 153 days.

(21) Appl. No.: 17/532,921

(22) Filed: Nov. 22, 2021

(65) Prior Publication Data

US 2022/0160997 A1  May 26, 2022

Related U.S. Application Data

(60) Provisional application No. 63/117,105, filed on Nov. 23, 2020.

(51) Int. Cl.
*A61M 25/01* (2006.01)
*A61M 25/00* (2006.01)
*A61M 25/06* (2006.01)

(52) U.S. Cl.
CPC .... *A61M 25/0108* (2013.01); *A61M 25/0026* (2013.01); *A61M 25/005* (2013.01);
(Continued)

(58) Field of Classification Search
CPC .......... A61M 25/0026; A61M 25/0108; A61M 25/007; A61M 2025/0037;
(Continued)

(56) References Cited

U.S. PATENT DOCUMENTS 5,308,318 A * 5/1994 Plassche, Jr. ......... A61M 27/00
604/540
6,056,743 A   5/2000 Ellis
(Continued)

FOREIGN PATENT DOCUMENTS

WO   WO-2020012075 A1 * 1/2020 ........ A61M 25/0009

OTHER PUBLICATIONS

International Search Report and Written Opinion dated Mar. 7, 2022 for International Application No. PCT/US2021/060389.
(Continued)

*Primary Examiner* — Courtney B Fredrickson
*Assistant Examiner* — Kayla M. Turkowski
(74) *Attorney, Agent, or Firm* — Seager, Tufte & Wickhem LLP

(57) ABSTRACT

A radiopaque anchor and delivery device system may comprise a pigtail catheter and a radiopaque anchor. The pigtail catheter may be a dual lumen catheter configured to deploy the radiopaque anchor and delivery a radiopaque fluid or contrast agent. The implantable radiopaque anchor may be slidably disposed within and deployable from a lumen of the elongate shaft. A method for deploying an implantable radiopaque anchor may include advancing a pigtail catheter through the vasculature to a target location; identifying an implant location; forming a channel in a tissue at the implant location; and deploying an implantable radiopaque anchor within the channel.

12 Claims, 23 Drawing Sheets

(52) U.S. Cl.
CPC .......... *A61M 25/007* (2013.01); *A61M 25/06* (2013.01); *A61M 2205/0266* (2013.01)

(58) Field of Classification Search
CPC .............. A61M 25/0028; A61M 25/00; A61M 25/0071; A61M 31/005; A61M 2039/0009; A61M 25/0029; A61B 2017/00783; A61B 90/39; A61B 2090/3991; A61B 6/481; A61F 2/2427
See application file for complete search history.

(56) References Cited

U.S. PATENT DOCUMENTS

| | | | |
|---|---|---|---|
| 7,041,097 B1* | 5/2006 | Webler | A61B 17/3403 606/41 |
| 8,613,706 B2 | 12/2013 | Langston | |
| 9,078,993 B2 | 7/2015 | Stinis | |
| 9,173,646 B2 | 11/2015 | Fabro | |
| 10,507,301 B2 | 12/2019 | Al-Jilaihawi | |
| 11,660,191 B2* | 5/2023 | Call | A61F 2/246 623/2.11 |
| 2002/0188167 A1* | 12/2002 | Viole | A61M 60/867 604/537 |
| 2002/0188170 A1 | 12/2002 | Santamore et al. | |
| 2002/0193782 A1 | 12/2002 | Ellis et al. | |
| 2003/0018358 A1* | 1/2003 | Saadat | A61B 18/24 606/232 |
| 2007/0144539 A1* | 6/2007 | van der Burg | A61B 17/0401 606/1 |
| 2008/0082136 A1* | 4/2008 | Gaudiani | A61B 6/481 607/9 |
| 2010/0145187 A1* | 6/2010 | Weber | A61M 25/01 53/396 |
| 2014/0046343 A1* | 2/2014 | Okazaki | A61M 25/09 606/130 |
| 2014/0046347 A1* | 2/2014 | Cully | A61B 17/11 606/151 |
| 2015/0351912 A1* | 12/2015 | Konstantino | A61B 17/12 600/38 |
| 2017/0028176 A1 | 2/2017 | Dam et al. | |
| 2018/0289926 A1* | 10/2018 | Haldis | A61M 25/0082 |
| 2019/0175196 A1 | 6/2019 | Guerra et al. | |
| 2019/0183628 A1 | 6/2019 | Prucell et al. | |
| 2019/0254678 A1 | 8/2019 | Dinges et al. | |
| 2020/0282183 A1 | 9/2020 | McConnell | |
| 2021/0085924 A1 | 3/2021 | McConnell et al. | |
| 2021/0178127 A1* | 6/2021 | Gerberding | A61M 25/09 |
| 2021/0290899 A1* | 9/2021 | Keränen | A61M 25/0009 |

OTHER PUBLICATIONS

Eng et al; "Mult-Pigtail Technique is Asociated with Decreased Contrast Use and Fluroscopic Adjustment for Transcatheter Aortic Valve Replacement", Structural Heart, pp. 1-29, 2019. DOI:10.1080/24748706.2019.1682211.

Iung et al; "A Prospective Survey of Patients with Valvular Heart Disease in Europe: The Euro Heart Survey on Valvular Heart Disease", European Heart Journal, vol. 24, pp. 1231-1243, 2003. Downloaded from https://academic.oup.com/article/24/13/1231/397045 by guest on Dec. 16, 2021.

* cited by examiner

RADIOPAQUE MARKER AND DELIVERY SYSTEM

CROSS REFERENCE TO RELATED APPLICATIONS

This application claims the benefit of and priority to U.S. Provisional Patent Application Ser. No. 63/117,105 filed on Nov. 23, 2020, the disclosure of which is incorporated herein by reference.

TECHNICAL FIELD

In general, the present disclosure relates to medical devices and delivery systems. And, more particularly, in certain embodiments, to a method and a system of radiopaque markers for use during an endovascular or cardiac procedure.

BACKGROUND

Transcatheter aortic valve replacement (TAVR) is used to treat aortic stenosis in a growing number of patients. To precisely deploy the TAVR valve, a clinician needs to get coplanar view (fluoroscopic perpendicular angle of deployment), which allows valve deployment in a 90° plane to the native annulus. The current practice is the placement of one, two, or even three pigtail catheters in the non-coronary cusp and/or right coronary cusp to serve as a landmark to guide the valve implant.

Further, some challenges associated with using one or more pigtail catheters to serve as landmarks during TAVR valve deployment include, but are not limited to: a need to ensure the pigtail catheter stays in place (e.g., is pushed against the nadir of the cusp(s)) for proper annulus plane identification, a need to use contrast injections for a good fluoroscopic view, and/or pigtail catheter placement in cusps can be somewhat obstructive during TAVR deployment.

According to the European Heart Survey on Valvular Heart Disease, 13.3% of patients with isolated, native left-sided valvular heart disease have pure aortic regurgitation (AI) (Iung, et al., Eur Heart J 2003; 24: 1231-1243). Left ventricular assist devices (LVAD) have become an important therapeutic option in patients with and developing end stage heart failure. However, up to 30% of patients with continuous-flow LVAD potentially develop significant AI within 3 years. A transcatheter solution would be highly valuable in above patient population given the high percentage that is inoperable. However, from a technical perspective, performing TAVR procedures in a patient with pure AI is still a challenging approach. There is poor visibility of the aortic valve on fluoroscopy due to a lack of calcium, which is an issue for positioning of the transcatheter valves, and a pigtail in the cusp will lose contrast due to regurgitation into the left ventricle.

The need thus remains for a system which provides for reliable and simple visualization of the aortic artery anatomy.

SUMMARY

The present invention provides a radiopaque marker and delivery system.

In a first example, a radiopaque anchor and delivery device system may comprise a pigtail catheter and an implantable radiopaque anchor. The pigtail catheter may include an elongate shaft extending from a proximal end to a distal end and defining a first lumen and a second lumen. The first lumen may extend distally from a proximal end and may be in fluid communication with one or more apertures extending through a side wall of the elongate shaft. The second lumen may extend distally from a proximal end and may be in fluid communication with at least one opening in the elongate shaft. The radiopaque anchor may be slidably disposed within the second lumen of the elongate shaft.

Alternatively or additionally to any of the examples above, in another example, the at least one opening in the elongate shaft may extend through the side wall of the elongate shaft.

Alternatively or additionally to any of the examples above, in another example, the at least one opening in the elongate shaft may be distally facing.

Alternatively or additionally to any of the examples above, in another example, the implantable radiopaque anchor may comprise a tubular body extending from a first end to a second end.

Alternatively or additionally to any of the examples above, in another example, the tubular body may include one or more radially extending barbs positioned adjacent to the second end thereof.

Alternatively or additionally to any of the examples above, in another example, the one or more radially extending barbs may be configured to anchor the implantable radiopaque anchor within a tissue.

Alternatively or additionally to any of the examples above, in another example, the implantable radiopaque anchor may comprise a proximal end region and a distal end region.

Alternatively or additionally to any of the examples above, in another example, the proximal end region may include one or more curved tines and the distal end region includes one or more curved tines.

Alternatively or additionally to any of the examples above, in another example, the tines may be movable between an expanded deployed configuration and a compressed delivery configuration.

Alternatively or additionally to any of the examples above, in another example, the proximal end region may comprise a woven structure including one or more filaments.

Alternatively or additionally to any of the examples above, in another example, the distal end region may comprise an elongate member extending distally from a distal end of the proximal end region.

Alternatively or additionally to any of the examples above, in another example, the implantable radiopaque anchor may comprise a helical body.

Alternatively or additionally to any of the examples above, in another example, the implantable radiopaque marker may comprise a biodegradable polymer doped with or carrying a radiopaque material.

Alternatively or additionally to any of the examples above, in another example, the implantable radiopaque anchor may be at least partially formed from a shape memory material.

Alternatively or additionally to any of the examples above, in another example, the system may further comprise a push member slidably disposed within the second lumen of the elongate shaft.

Alternatively or additionally to any of the examples above, in another example, the system may further comprise a guidewire slidably disposed within the second lumen of the elongate shaft.

In another example, a radiopaque anchor and delivery device system may comprise a pigtail catheter and an implantable radiopaque anchor. The pigtail catheter may comprise an elongate shaft extending from a proximal end to a distal end. The elongate shaft may define a first lumen extending distally from a proximal end and in fluid communication with one or more apertures extending through a side wall of the elongate shaft. The elongate shaft may also define a second lumen extending distally from a proximal end and in fluid communication with at least one opening in the elongate shaft. The system may further include a guidewire slidably disposed within the second lumen of the elongate shaft and a push member slidably disposed within the second lumen of the elongate shaft and over the guidewire. The implantable radiopaque anchor may be slidably disposed over the guidewire and within the second lumen of the elongate shaft. Distal actuation of the push member may be configured to deploy the implantable radiopaque anchor from the second to lumen.

Alternatively or additionally to any of the examples above, in another example, the implantable radiopaque anchor may comprise a tubular body extending from a first end to a second end.

Alternatively or additionally to any of the examples above, in another example, the tubular body may include a first radially extending barb and a second radially extending barb positioned adjacent to the second end thereof.

Alternatively or additionally to any of the examples above, in another example, the cross-sectional profile of the implantable radiopaque anchor may increase in a distal to proximal direction a long a length of the first and second radially extending barbs.

In another example, a method for deploying an implantable radiopaque anchor may comprise advancing a pigtail catheter through the vasculature to a target location, identifying an implant location, forming a channel in a tissue at the implant location, and deploying an implantable radiopaque anchor within the channel.

Alternatively or additionally to any of the examples above, in another example, identifying an implant location may include administering a radiopaque fluid or contrast agent adjacent to the target location.

Alternatively or additionally to any of the examples above, in another example, deploying an implantable radiopaque anchor within the channel may comprise distally actuating the implantable radiopaque anchor through a lumen of the pigtail catheter.

In another example, a system for guiding implant depth may comprise a pigtail catheter and an elongate wire. The pigtail catheter may comprise an elongate shaft extending from a proximal end to a distal end and defining a first lumen extending distally from a proximal end and a second lumen extending distally from a proximal end. The first lumen may be in fluid communication with one or more apertures extending through a side wall of the elongate shaft. The second lumen may be in fluid communication with at least one opening in the elongate shaft. The elongate wire may include a plurality of radiopaque markers disposed adjacent a distal end region thereof and be slidably disposed within the second lumen of the elongate shaft.

Alternatively or additionally to any of the examples above, in another example, the at least one opening in the elongate shaft may extend through the side wall of the elongate to shaft.

Alternatively or additionally to any of the examples above, in another example, the at least one opening in the elongate shaft may be distally facing.

Alternatively or additionally to any of the examples above, in another example, the radiopaque markers may be uniformly spaced along the distal end region of the elongate wire.

Alternatively or additionally to any of the examples above, in another example, a distal end of the elongate wire may comprise a needle.

Alternatively or additionally to any of the examples above, in another example, the system may further comprise a locking mechanism at the proximal end of the elongate shaft. The locking mechanism may be configured to secure the elongate wire relative to the elongate shaft.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
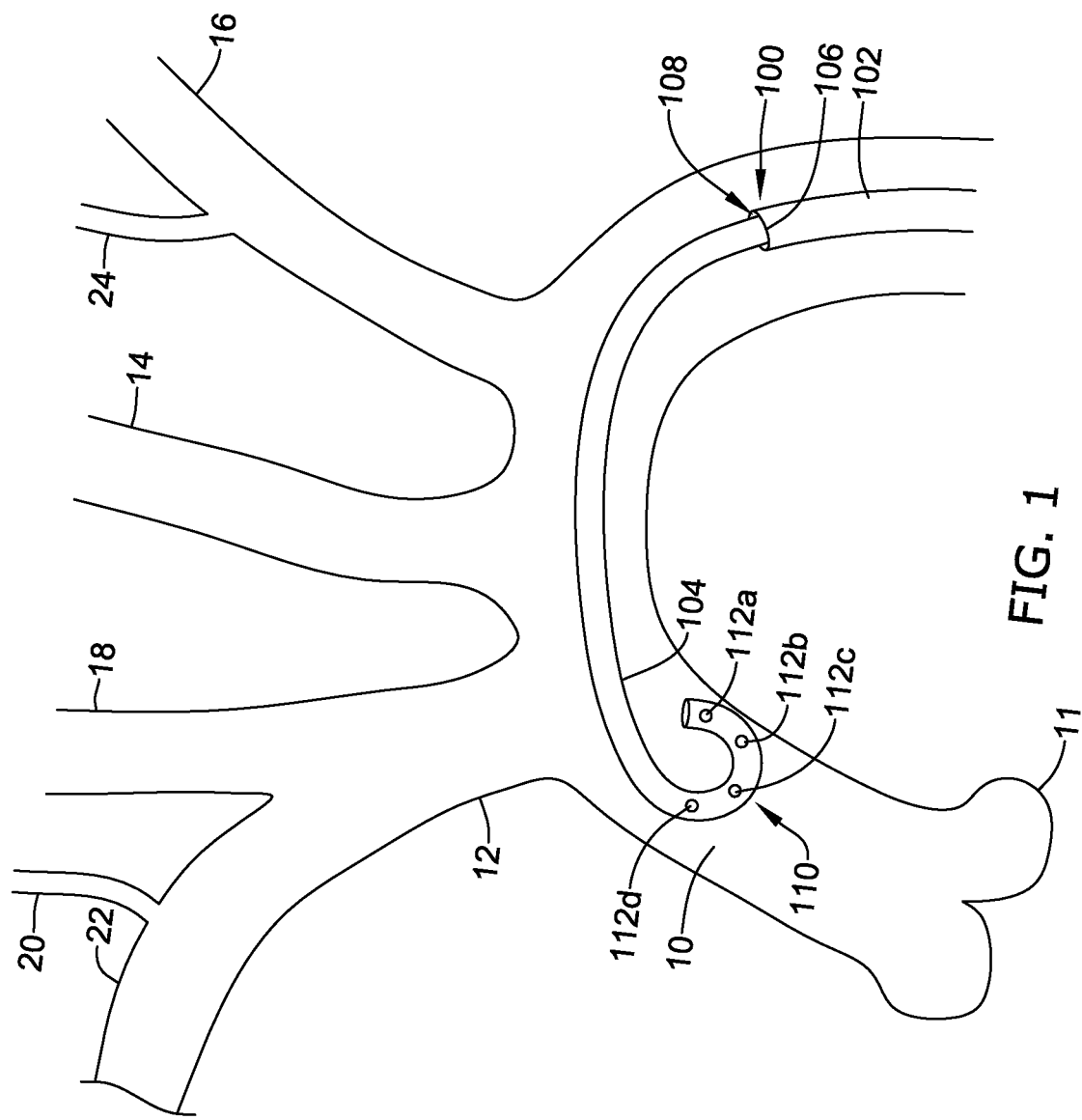
FIG. 1 is a schematic view of an aortic arch including an illustrative delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimension ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Transcatheter aortic valve replacement (TAVR) is used to treat aortic stenosis in a growing number of patients. To precisely deploy the TAVR valve, a clinician needs to have a coplanar view (fluoroscopic perpendicular angle of deployment), which allows valve deployment in a 90° plane to the native annulus (formed by hinge points or nadir of the valve cusps). Precise deployment of the valve is important because if the valve is deployed too low the valve may leak and if the valve is deployed too high the valve may damage the coronary arteries. Further, the depth of the implant may be correlated with the likelihood of a permanent pacemaker implant post-TAVR. However, identification of the native annulus may be difficult due to the soft tissue. The current practice includes the placement of one, two, or even three pigtail catheters in the non-coronary cusp and/or right coronary cusp to serve as a landmark to guide the valve implant. However, some challenges associated with using one or more pigtail catheters to serve as landmarks during TAVR valve deployment include, but are not limited to, a need to ensure the pigtail catheter stays in place for proper annulus plane identification (e.g., pushed against the nadir (e.g., attachment points) of the cusp(s)), a need to use contrast injections for a good fluoroscopic view, and/or pigtail catheter placement in cusps can be somewhat obstructive during TAVR deployment (e.g., obstructs the delivery of the TAVR valve). While the disclosure is described with respect to TAVR procedures, it should be understood that the devices and methods described herein are not only to TAVR procedures. The devices and methods described herein can be used in any other procedure where visualization is desired.

The disclosure generally relates to devices and methods for visualization of the aortic anatomy (and/or other anatomy as applicable) as well as devices and method for better controlling implant depth. In some cases, radiopaque markers can be delivered before and/or during an endovascular procedure (e.g., transcatheter aortic valve implantation (TAVI) or replacement (TAVR), transcatheter mitral valve implantation (TAMI) or replacement (TAMR), surgical aortic valve replacement (SAVR), thoracic endovascular aortic repair (TEVAR), other surgical valve repair, implantation, or replacement, to facilitate precise deployment or repair of a valve or other anatomy. In yet other cases, radiopaque markers can be delivered before and/or during procedures in other parts of the body.

FIG. 1 is a schematic view of an aortic arch 10 including a delivery system 100 for delivering an implantable radiopaque marker and/or a replacement valve. The aortic arch 10 is downstream of the aortic valve 11. The aortic arch 10 typically includes three great branch arteries: the brachiocephalic artery or innominate artery 12, the left common carotid artery 14, and the left subclavian artery 16. The innominate artery 12 branches to the right carotid artery 18, then the right vertebral artery 20, and thereafter is the right subclavian artery 22. The right subclavian artery 22 supplies blood to and may be directly accessed from the right arm (termed right radial access). The left subclavian artery 16 branches to the left vertebral artery 24, usually in the shoulder area. The left subclavian artery 16 supplies blood to and may be directly accessed from the left arm (termed left radial access).

The delivery system 100 may include an outer sheath 102 and a pigtail catheter 104. The outer sheath 102 includes a proximal end (not explicitly shown) and a distal end 106. The proximal end is configured to be held and manipulated by a user such as a surgeon. In some cases, the proximal end may be coupled to a handle configured to facilitate delivery and deployment of the outer sheath 102. The outer sheath 102 may define a lumen 108 extending from the proximal end to the distal end 106 thereof. The lumen 108 may be configured to slidably receive the pigtail or angiography catheter 104, a filter device (for protecting the cerebral vasculature), and/or a procedural catheter (such as, but not limited to a TAVR or TAVI procedural catheter or device), etc. The pigtail catheter 104 may be radially inward of the outer sheath 102 which may have a diameter large enough for a procedural catheter to pass therethrough. The outer sheath 102 may comprise an atraumatic distal tip. In some cases, the outer sheath 102 may be flexible and/or atraumatic. The outer sheath 102 may comprise a curvature, for example based on an intended placement location (e.g., the left subclavian artery 16 and/or the aortic arch 10). Alternatively, or additionally, the outer sheath 102 may be steerable.

The right femoral artery may be accessed using an introducer. The outer sheath 102 is steered, into or towards the aortic arch 10. In some cases, the outer sheath 102 may be advanced over a guidewire, although this is not required. In some implementations, the guidewire and the outer sheath 102, pigtail catheter 104, and/or other devices may be tracked together, with the guidewire leading the outer sheath 102 (e.g., advance the guidewire a distance, then advance the outer sheath 102 over the guidewire approximately the same distance). In some cases, where the guidewire is floppy or lacks rigidity, it may be introduced inside the outer sheath 102 and then advanced ahead of other devices in the vasculature.

The outer sheath 102 may be advanced into the descending portion of the aortic arch 10. The pigtail catheter 104 is then advanced through the outer sheath 102 (if it was not advanced with the outer sheath 102). In some embodiments, the pigtail catheter 104 may be advanced into the ascending portion of the aortic arch 10 where it may deliver a radiopaque fluid or contrast fluid to facilitate visualization of the procedure. In other embodiments, the pigtail catheter 104 may be positioned at or against the cusps or leaflets of the aortic valve 11. Alternatively, or additionally, the pigtail catheter 104 is used to deliver an implantable radiopaque marker, as will be described in more detail herein. A distal end region 110 of pigtail catheter 104 may have a generally arcuate shape (although this is not required) and include one or more apertures 112a, 112b, 112c, 112d (collectively, 112) therein. The one or more apertures 112 may be in fluid communication with a lumen of the pigtail catheter 104 and may be configured to deliver the radiopaque fluid or contrast fluid. Tracking of the delivery system 100 may be performed under fluoroscopy, for example using radiopaque markers (e.g., at a distal end of the outer sheath 102) and/or radiopaque fluid or contrast media. Radiopaque fluid or contrast media may be provided through the pigtail catheter 104 and/or the outer sheath 102.

Figure 2:
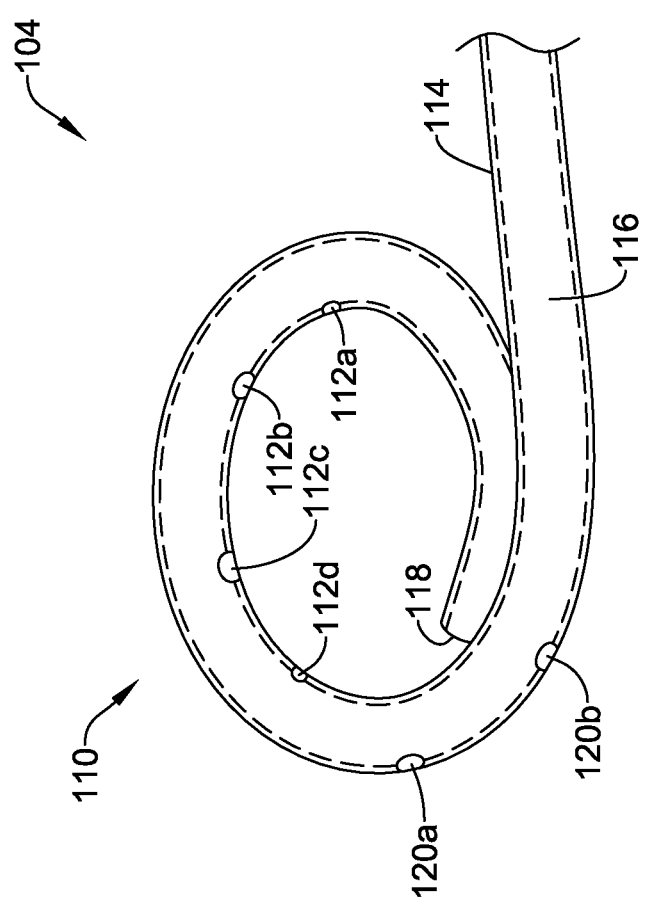
FIG. 2 is a perspective view of a distal end region of an illustrative pigtail catheter.

FIG. 2 is an enlarged perspective view of the distal end region 110 of the illustrative pigtail catheter 104. The pigtail catheter 104 includes a tubular elongate shaft 114 extending from a proximal end configured to remain outside the body to the distal end region 110. The elongate shaft 114 includes at least one lumen 116 extending from the proximal end thereof to the distal end region 110. In some cases, the lumen 116 may terminate proximal to the distal end 118 of the elongate shaft 114 while in other cases, the lumen 116 may extend to the distal end 118 to define a distal opening (not explicitly shown). In some embodiments, the elongate shaft 114 may include more than one lumen 116. When so provided, the two or more lumens may be arranged in a side by side or collinear arrangement, in a coaxial or tube within a tube arrangement, or combinations thereof. It is further contemplated that when so provided, the two or more lumens may be fluidly isolated from one another.

In the absence of an external biasing force, or in a deployed configuration, the distal end region 110 is configured to assume a curved pigtail or J shape. It is contemplated that the distal end region 110 may have any degree of curvature desired including less than 360° or greater than 360°, as desired. The distal end region 110 may be biased into a generally linear, or delivery, configuration by, for example, a guidewire or stiffening member slidably disposed within the lumen 116 or a stiffer tube (such as, but not limited to, an outer sheath 102) disposed over an outer surface of the pigtail catheter 104. These are just examples and are not intended to limit the pigtail catheter 104 to a particular configuration.

The pigtail catheter 104 includes a first set of holes or apertures 112 and a second set of holes or apertures 120a, 120b (collectively, 120). The first set of apertures 112 may include one, two, three, four, or more apertures, as desired. Similarly, the second set of apertures 120 may include one, two, three, four, or more apertures, as desired. The first set of apertures 112 may be in fluid communication with a radiopaque fluid source and/or a contrast fluid source. The second set of apertures 120 may be configured to deploy an implantable radiopaque marker from the lumen 116 of the pigtail catheter 104 and into the body of a patient. For example, the implantable radiopaque markers may be pushed out of at least one aperture 120a, 120b and into the nadir of a cusp of the aortic valve using a stiff guidewire, or other pushing element, as will be described in more detail herein.

In some cases, the first set of apertures 112 may be positioned on the elongate shaft 114 such that when the distal end region 110 of the pigtail catheter 104 is in the deployed configuration, the first set of apertures 112 are positioned or directed radially inwards relative to the curve of the distal end region 110 (or on the concave surface thereof). However, this is not required. In some cases, the first set of apertures 112 may be positioned on the elongate shaft 114 such that when the distal end region 110 of the pigtail catheter 104 is in the deployed configuration the first set of apertures 112 are positioned or directed radially outwards (not explicitly shown) relative to the curve of the distal end region 110 (or on the convex surface thereof). It is contemplated that the position of the first set of apertures 112 is not limited to the radially inward or outward surface of the distal end region 110. It is contemplated that the first set of apertures 112 may be positioned at any circumferential location about the elongate shaft 114, or combinations of circumferential locations, as desired.

In some cases, the second set of apertures 120 may be positioned on the elongate shaft 114 such that when the distal end region 110 of the pigtail catheter 104 is in the deployed configuration, the second set of apertures 120 are positioned or directed radially outwards relative to the curve of the distal end region 110 (or on the convex surface thereof). However, this is not required. In some cases, the second set of apertures 120 may be positioned on the elongate shaft 114 such that when the distal end region 110 of the pigtail catheter 104 is in the deployed configuration the second set of apertures 120 are positioned or directed radially inwards (not explicitly shown) relative to the curve of the distal end region 110 (or on the concave surface thereof). It is contemplated that the position of the second set of apertures 120 is not limited to the radially inward or outward surface of the distal end region 110. It is contemplated that the second set of apertures 120 may be positioned at any circumferential location about the elongate shaft 114, or combinations of circumferential locations, as desired.

Figure 3:
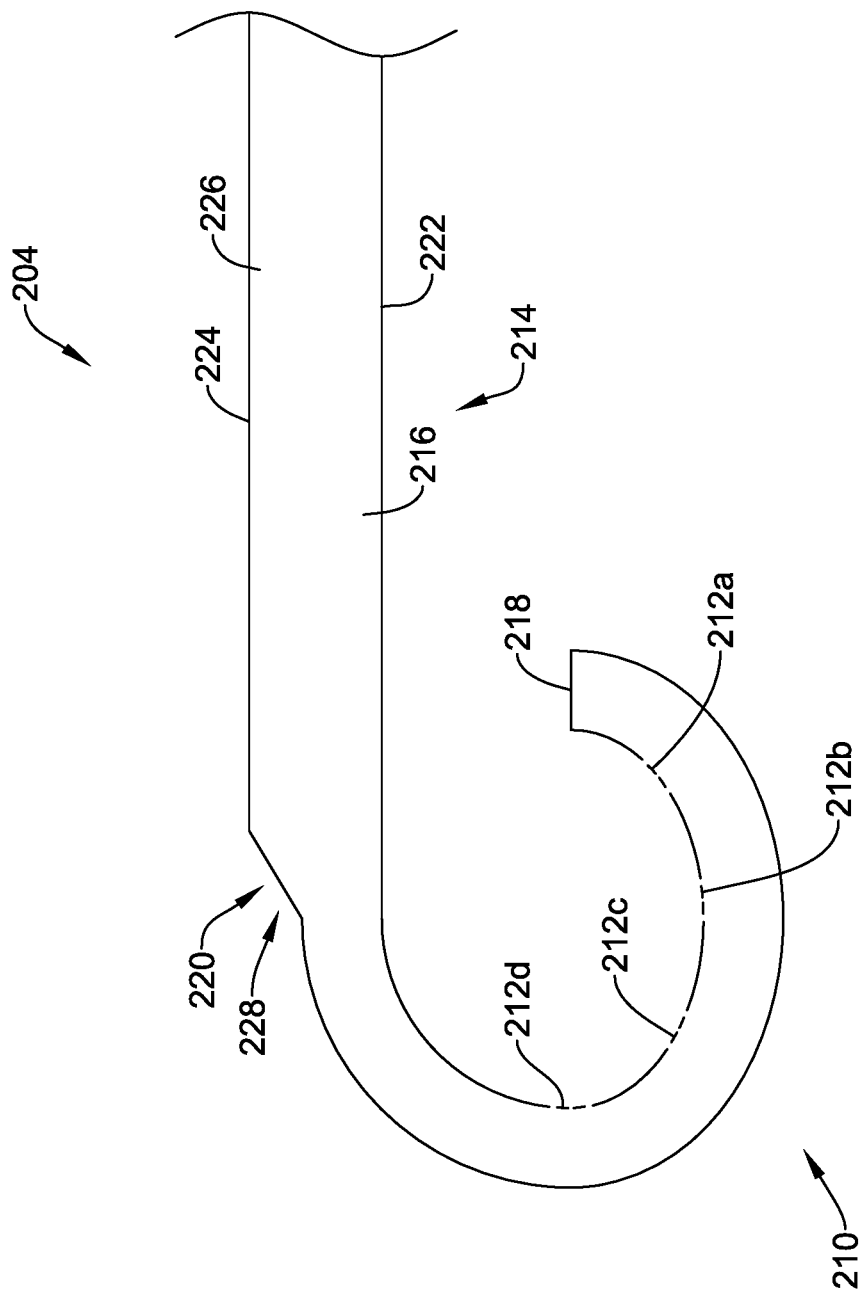
FIG. 3 is an enlarged partial side view of another illustrative pigtail catheter.

FIG. 3 is an enlarged partial side view of another illustrative pigtail catheter 204. The pigtail catheter 204 includes a tubular elongate shaft 214 extending from a proximal end configured to remain outside the body to the distal end region 210. The elongate shaft 214 includes at least a first lumen 216 configured to deliver a radiopaque fluid and/or a contrast fluid and a second lumen 226 configured to deliver an implantable radiopaque marker. The two or more lumens 216, 226 may be arranged in a side by side or collinear arrangement, in a coaxial or tube within a tube arrangement, or combinations thereof. The two or more lumens 216, 226 may be fluidly isolated from another The elongate shaft 214 may include a first portion 222 defining the first lumen 216 and a second portion 224 defining the second lumen 226. It is contemplated that the first and second portions 222, 224 need not have the same length as each other. In some embodiments, the elongate shaft 214 may be extruded as a single monolithic structure to form side-by-side lumens 216, 226. In other embodiments, the elongate shaft 214 may be formed by other suitable means, such as a first and a second separate extruded tubes arranged side-by-side and connected by adhesive, or the like.

The first lumen 216 may extend from the proximal end of the first portion 222 towards a distal end 218 thereof. In some cases, the first lumen 216 may terminate proximal to the distal end 218 of the first portion 222 while in other cases, the first lumen 216 may extend to the distal end 218 to define a distal opening (not explicitly shown). The second lumen 226 may extend from the proximal end of the second portion 224 towards a distal end 228 thereof. The second lumen 226 may extend to the distal end 228 to define a distal opening 220 (e.g., distally facing). However, this is not required. In some cases, the second lumen 226 may terminate proximal to the distal end 228. In such an instance, a side port may be provided to allow an implantable radiopaque marker to be advanced through and exit the second lumen 226.

In the absence of an external biasing force, or in a deployed configuration, the distal end region 210 is configured to assume a curved pigtail or J shape. It is contemplated that the distal end region 210 may have any degree of curvature desired including less than 360° or greater than 360°, as desired. The distal end region 210 may be biased into a generally linear or delivery configuration by for example, a guidewire or stiffening member slidably disposed within the lumen 216 or a stiffer tube (such as, but not limited to an outer sheath) disposed over an outer surface of the pigtail catheter 204. These are just examples and are not intended to limit the pigtail catheter 204 to a particular configuration.

The first portion 222 includes a set of holes or apertures 212a, 212b, 212c, 212d (collectively, 212). The set of apertures 212 may include one, two, three, four, or more apertures, as desired. The set of apertures 212 may be in fluid communication with a radiopaque fluid source and/or a contrast fluid source. As described herein, the second portion 224 may include a distal opening 220 through which an implantable radiopaque marker is deployable. For example, the implantable radiopaque markers may be pushed out of the distal opening 220 and into the nadir of a cusp of the aortic valve using a stiff guidewire, or other pushing element, as will be described in more detail herein.

In some cases, the set of apertures 212 may be positioned on the first portion 222 such that when the distal end region 210 of the pigtail catheter 204 is in the deployed configuration, the set of apertures 212 are positioned or directed radially inwards relative to the curve of the distal end region 210 (or on the concave surface thereof). However, this is not required. In some cases, the first set of apertures 212 may be positioned on the elongate shaft 214 such that when the distal end region 210 of the pigtail catheter 204 is in the deployed configuration the first set of apertures 212 are positioned or directed radially outwards (not explicitly shown) relative to the curve of the distal end region 210 (or on the convex surface thereof). It is contemplated that the position of the set of apertures 212 is not limited to the radially inward or outward surface of the distal end region 210. It is contemplated that the set of apertures 212 may be positioned at any circumferential location about the portion 222, or combinations of circumferential locations, as desired.

Figure 4:
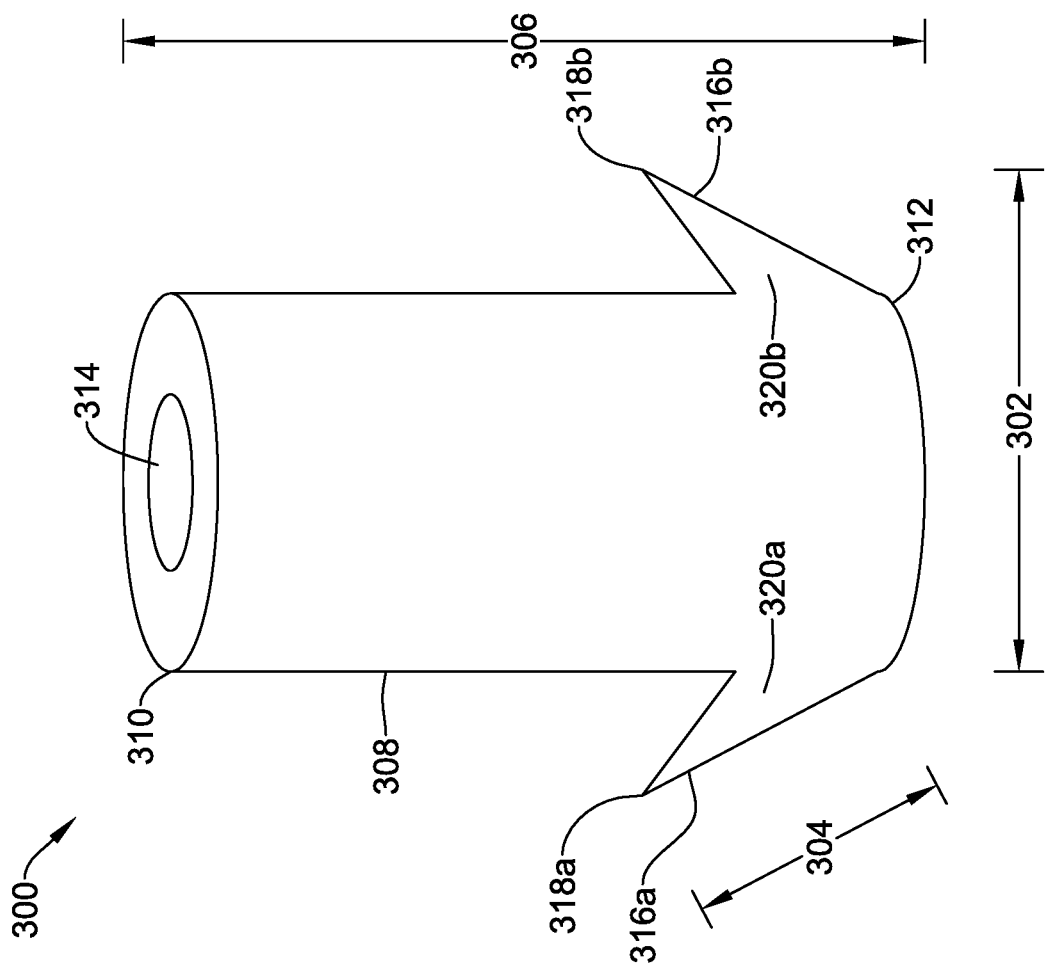
FIG. 4 is a perspective view of an illustrative implantable radiopaque anchor.

FIG. 4 is a perspective view of an illustrative implantable radiopaque marker or anchor 300. The radiopaque anchor 300 is configured to be implanted in the nadir (hinge point) of the non-coronary, right coronary, and/or left-coronary cusps to serve as markers for identification of the proper plane for valve deployment. However, the radiopaque anchor 300 may be used in other anatomical locations for different procedures, as desired. The radiopaque anchor 300 may have a width 302 and/or depth 304 in the range of about 0.5 millimeters (mm) to about 2.0 mm, about 0.75 mm to about 1.75 mm, or about 1.0 to about 1.5 mm. In some cases, the radiopaque anchor 300 may have a width 302 and/or depth 304 of less than 0.5 mm or greater than 2.0 mm, as desired. The radiopaque anchor 300 may have a height 306 in the range of about 0.5 millimeters (mm) to about 3.0 mm, about 1.0 mm to about 2.5 mm, or about 1.5 to about 2.0 mm. In some cases, the radiopaque anchor 300 may have a height 306 of less than 0.5 mm or greater than 3.0 mm, as desired. It is contemplated that the size of the radiopaque anchor 300 may be determined based on the anatomical location it will be implanted.

The radiopaque anchor 300 has a generally tubular body 308 extending from a first or proximal end 310 to a second or distal end 312. The radiopaque anchor 300 may be formed entirely from a radiopaque material, such as, but not limited to, tantalum or platinum iridium. In some cases, the radiopaque anchor 300 may be formed from a non-radiopaque material and may be coated with, doped with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 300 may be made radiopaque. Other materials and/or techniques may be used as desired.

The body 308 may have a generally circular cross-sectional shape, although other shapes may be used as desired. A lumen 314 may extend from the proximal end 310 to the distal end 312. The lumen 314 may be sized and shaped such that the radiopaque anchor 300 may be advanced over a guidewire or other lead wire (not explicitly shown). The radiopaque anchor 300 further includes one or more radially extending barbs 316a, 316b (collectively, 316). The barbs 306 may be generally uniformly positioned or equally spaced about the circumference of the body 308, although this is not required. In some cases, the barbs 306 may be eccentrically spaced. The radiopaque anchor 300 may include fewer than two or more than two barbs 316, as desired. In some cases, the radiopaque anchor 300 may include a single barb 316 that extends about an entirety or less than an entirety of the circumference of the body 308. The barbs 316a, 316b each include a proximal end 318a, 318b (collectively, 318) radially spaced from the body 308 and a distal end 320a, 320b (collectively, 320) in contact with the body 308. For example, over a length of the barbs 316, the overall cross-sectional dimension increases in the distal to proximal direction. In some embodiments, the barbs 316 may be formed as a single monolithic structure with the body 308. In other embodiments, the barbs 316 may be formed as separate structures from the body 308 and subsequently attached, coupled or otherwise affixed thereto.

In some cases, the proximal ends 318 of the barbs 316 may be configured to deflect radially inwards to facilitate distal advancement of the radiopaque anchor 300 through a delivery device (such as, but not limited to a pigtail catheter such as those described herein), although this is not required. The distal end 312 of the radiopaque anchor 300 is configured to lead the radiopaque anchor 300 as it is advanced through the delivery device into the bodily tissue. The barbs 316 are angled or sloped such that the radiopaque anchor 300 is easily distally advanced through the tissue but proximal retraction of the radiopaque anchor 300 is difficult or precluded. This may help ensure that once the radiopaque anchor 300 is implanted into the tissue it is self-anchoring. The angle and/or length of the barbs 316 may be varied It is contemplated that the barbs 316 may have structures or shapes different from an angled surface, including, but not limited to, curves, steps, etc. It is contemplated that other structural features in place of or in addition to the barbs 316 may be used to help secure the radiopaque anchor 300 within the tissue.

Figure 5:
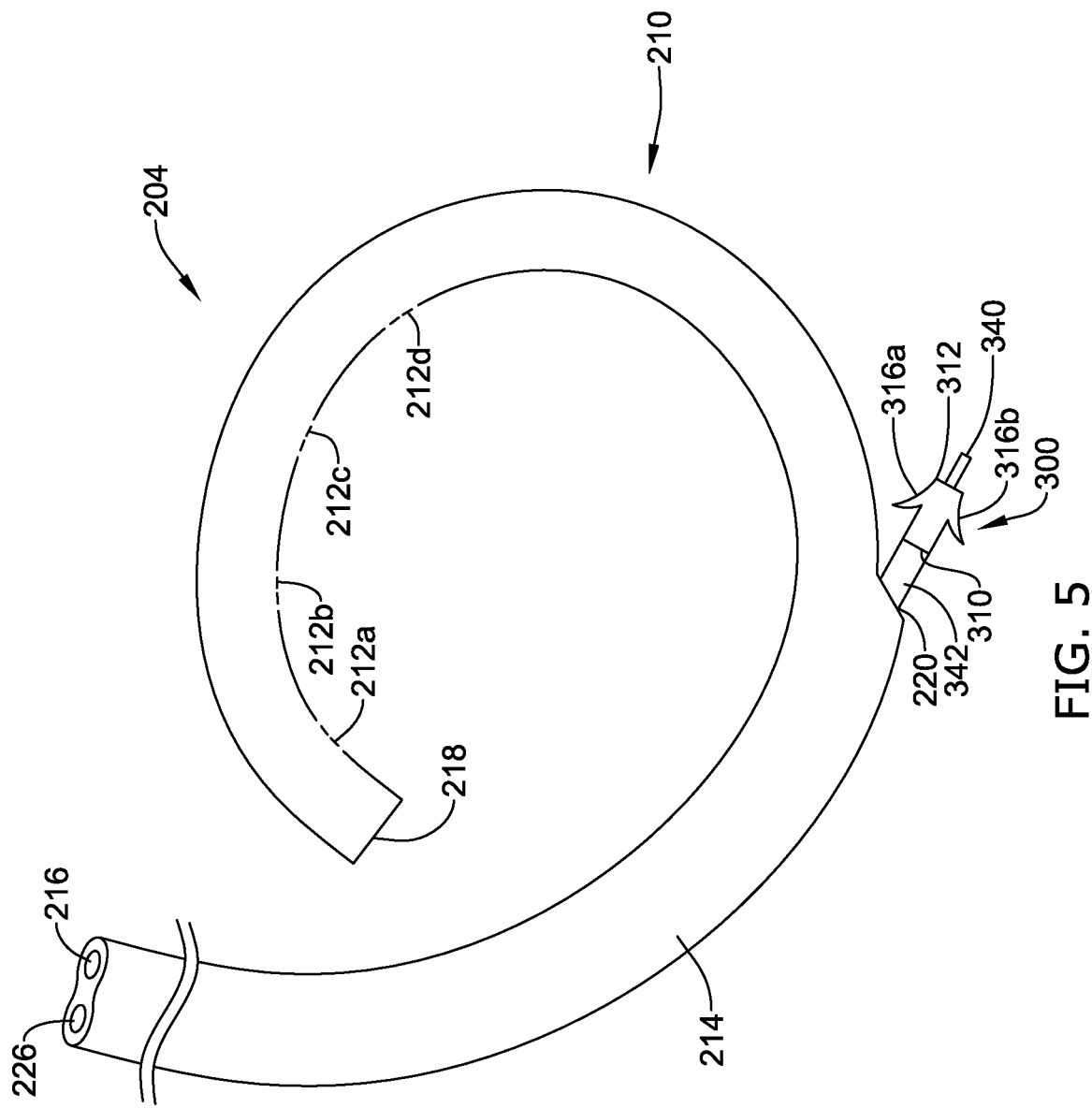
FIG. 5 is a partial side view of the illustrative radiopaque anchor of FIG. 4 extending from the illustrative pigtail catheter of FIG. 3.

FIG. 5 is a partial side view of the illustrative radiopaque anchor 300 extending from an illustrative pigtail catheter 204. While the radiopaque anchor 300 is shown and described with an illustrative pigtail catheter 204, it should be understood that the radiopaque anchor 300 may be delivered using other pigtail catheters, such as, but not limited to, the pigtail catheter 104 described herein, or other delivery devices or systems, as desired.

The radiopaque anchor 300 is loaded into the second lumen 226 of the pigtail catheter 204 via a proximal opening (not explicitly shown). In some cases, the radiopaque anchor 300 may be loaded over or slidably disposed over a guidewire 340 received within the second lumen 226. In some cases, the guidewire 340 may be advanced into the second lumen 226 prior to loading the radiopaque anchor 300 onto the guidewire 340. In other cases, the radiopaque anchor 300 may be loaded onto the guidewire 340 prior to advancing the guidewire 340 and the radiopaque anchor 300 into the lumen 226 of the pigtail catheter 204. Once the radiopaque anchor 300 is disposed within a proximal portion of the second lumen 226, a delivery tube or push member 342 contacts the distal end 310 of the radiopaque anchor 300 and pushes or distally advances the radiopaque anchor 300 through the second lumen 226 over the guidewire 340 towards the distal opening 220. In some cases, the guidewire 340 and the push member 342 may be advanced concurrently or in succession (e.g., with the guidewire 340 leading the push member 342), as desired. It is contemplated that the radiopaque anchor 300, guidewire 340 and/or push member 342 may be at least partially advanced through the second lumen 226 prior to advancing the pigtail catheter 204 within the vasculature. In other instances, the radiopaque anchor 300, guidewire 340 and/or push member 342 may be advanced through the second lumen 226 after the pigtail catheter 204 has been advanced through the vasculature and is positioned at or near a target location within the body.

To deploy the radiopaque anchor 300 within the body, the pigtail catheter 204 may be advanced through an outer sheath introduced into the right femoral artery, although other access points may be used as desired. The pigtail catheter 204 may be advanced through the outer sheath to the desired treatment location. In the case of a TAVR procedure, the pigtail catheter 204 may be advanced into the ascending aorta or adjacent to the aortic valve. Once the pigtail catheter 204 is in position a radiopaque fluid and/or contrast agent may be delivered to the anatomy adjacent to the distal end region 210 through the first lumen 216 and the set of apertures 212. The radiopaque fluid and/or contrast agent may be used to identify the cusps of valve and one or more implant locations for one or more radiopaque anchors 300. The pigtail catheter 204 may then be oriented such that the distal opening 220 of the second lumen 226 is aligned with the desired implant location.

Figure 6A:
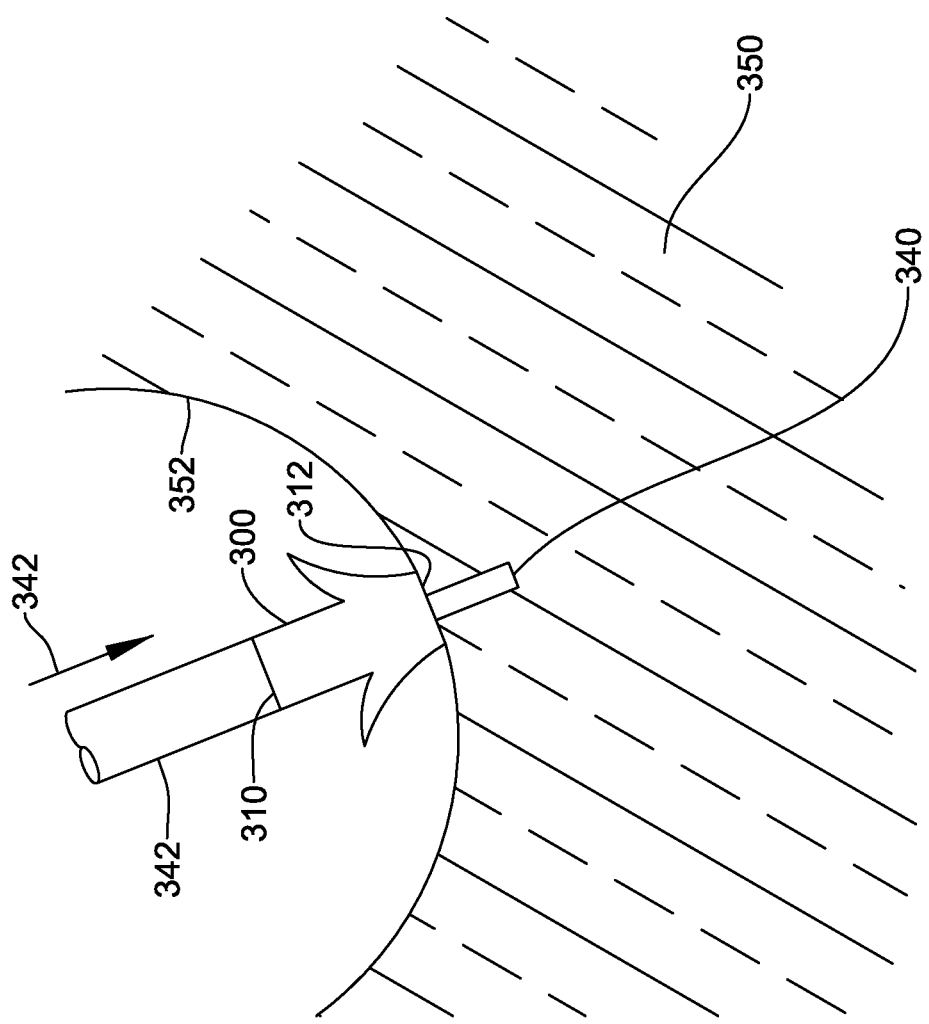
FIGS. 6A-6C illustrate an illustrative radiopaque anchor in sequential stages of delivery.
Figure 6B:
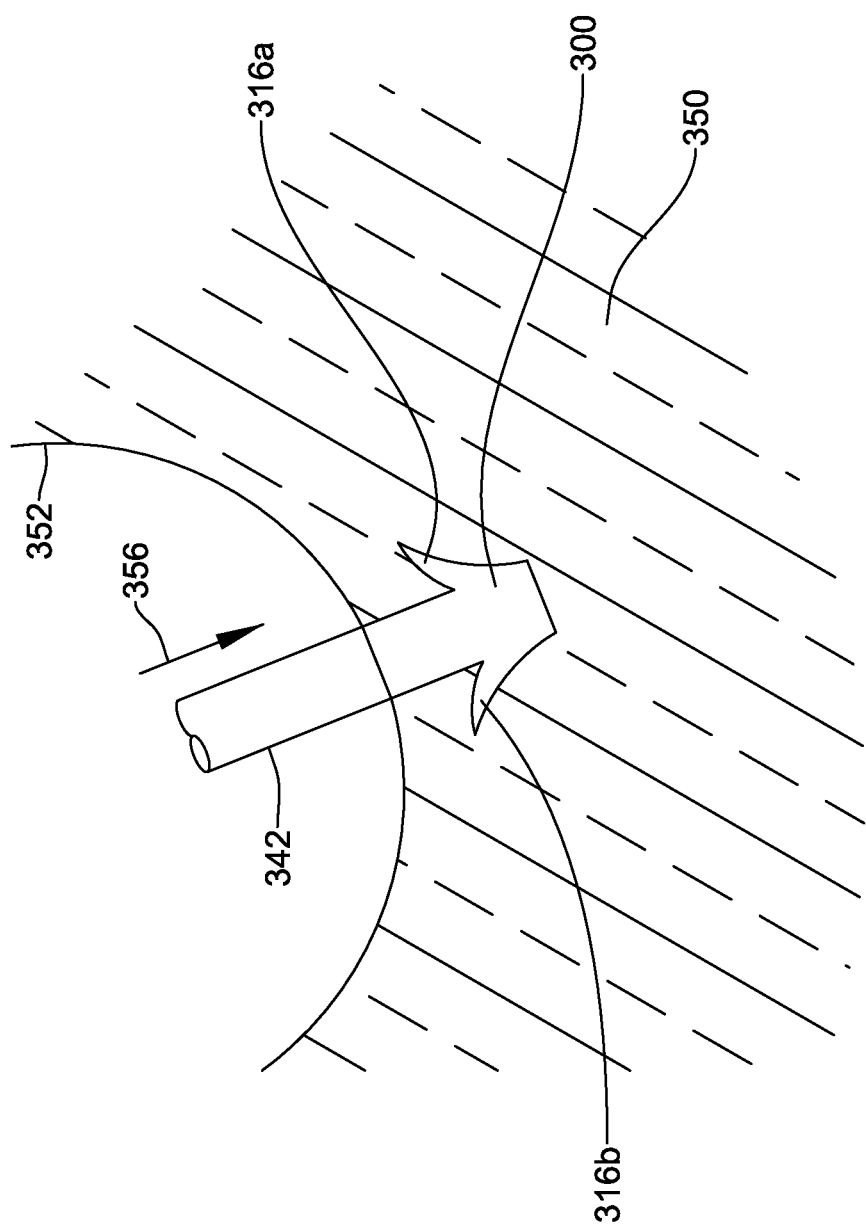
Figure 6C:
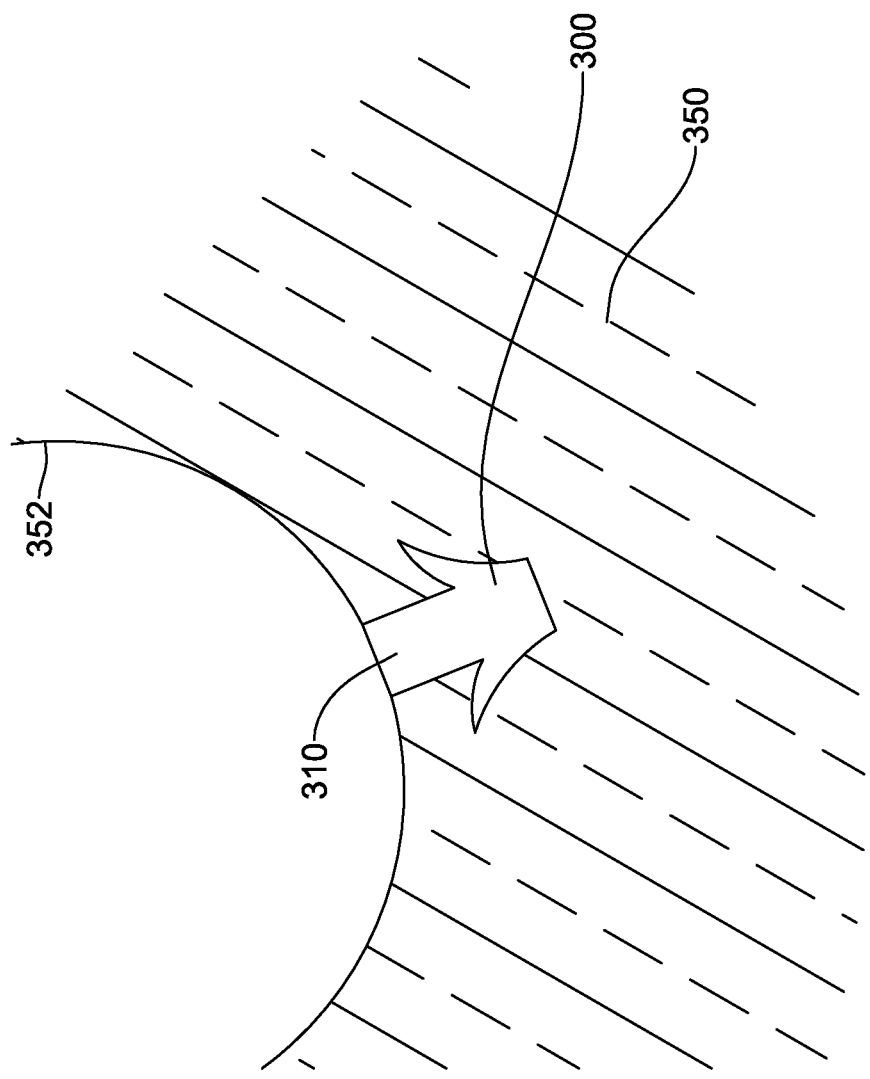

Referring now to FIGS. 6A-6C, which illustrate the radiopaque anchor 300 in sequential stages of delivery, once the pigtail catheter 204 is in position the radiopaque anchor 300 is distally advanced from the distal opening 220. In FIGS. 6A-6C, the pigtail catheter 204 is not shown to more particularly illustrate the relationship between the radiopaque anchor 300, the guidewire 340, and the push member 342. However, it should be understood that the radiopaque anchor 300 is distally advanced from a lumen of a delivery device, although other delivery methods may be used. Once the pigtail catheter 204 is in position, the guidewire 340 may be distally advanced, as shown at arrow 354 so that it penetrates the target tissue 350 (e.g., the left coronary cusp, right coronary cusp, and/or non-coronary cusp in the case of TAVR). In some cases, the guidewire 340 may include radiopaque markers (not explicitly shown) or include radiopaque material to allow the implant location of the radiopaque anchor 300 to be verified prior to embedding the radiopaque anchor 300 in tissue. Alternatively, or additionally, the distal end 312 of the radiopaque anchor 300 may be brought into contact (e.g., through distal actuation of the push member 342) with the surface 352 to the tissue 350 to verify the implant location is correct or accurate. The push member 342 may then be used to distally advance the radiopaque anchor 300 over the guidewire 340 and into the tissue 350, as shown in FIG. 6B. The angle of the barbs 316 facilitates distal movement of the radiopaque anchor 300 into the tissue 350 and precludes or limits dislodgement (e.g., proximal movement) of the radiopaque anchor 300.

Once the radiopaque anchor 300 is anchored within the tissue 350, the guidewire 340, push member 342, and pigtail catheter 204 can be proximally retracted, as shown in FIG. 6C. In some cases, the guidewire 340, push member 342, and/or pigtail catheter 204 may be fully removed from body. In other cases, the guidewire 340, push member 342, and/or pigtail catheter 204 may be proximally retracted but remain in the body (e.g., displaced from the area of valve implantation). In some cases, the radiopaque anchor 300 may be implanted within the tissue 350 such that the proximal end 310 thereof is fully within the tissue 350 (not explicitly shown). In other embodiments, the radiopaque anchor 300 may be implanted within the tissue 350 such that the proximal end 310 thereof is flush with or about at the surface 352 of the tissue 350. In yet other embodiments, the radiopaque anchor 300 may be implanted within the tissue 350 such that the proximal end 310 thereof extends from the surface 352 of the tissue 350 (not explicitly shown). Once the radiopaque anchor 300 has been delivered, the pigtail catheter 204 may be used to deliver one or more additional radiopaque anchors 300 to one or more additionally locations. For example, one or more radiopaque anchors 300 may be delivered to each cusp to improve visualization of the anatomy under fluoroscopy. In other cases, a radiopaque anchor 300 may be positioned in each cusp. It is further contemplated that more than one dual lumen pigtail catheter may be used to deploy radiopaque anchors 300 in each cusp simultaneously or substantially simultaneously.

It is contemplated that the implantation of one or more radiopaque anchors 300 may reduce contrast injections within the patient. For example, once the radiopaque anchors 300 are positioned, the radiopaque anchors 300 are able to provide beacons for positioning of the TAVR valve. Further, as the pigtail catheter is not necessary for contrast injections after implantation of the radiopaque anchors 300, the pigtail catheter (or other delivery system) can be removed from the anatomy which may help facilitate delivery of the TAVR valve (e.g., fewer devices are in the vasculature during delivery of the TAVR valve). Additionally, the radiopaque anchors 300 may enable better visualization of the annulus plane during implantation of the valve while clearly identifying the orientation of the radiopaque anchor 300 relative to the annular plane of the valve.

Figure 7:
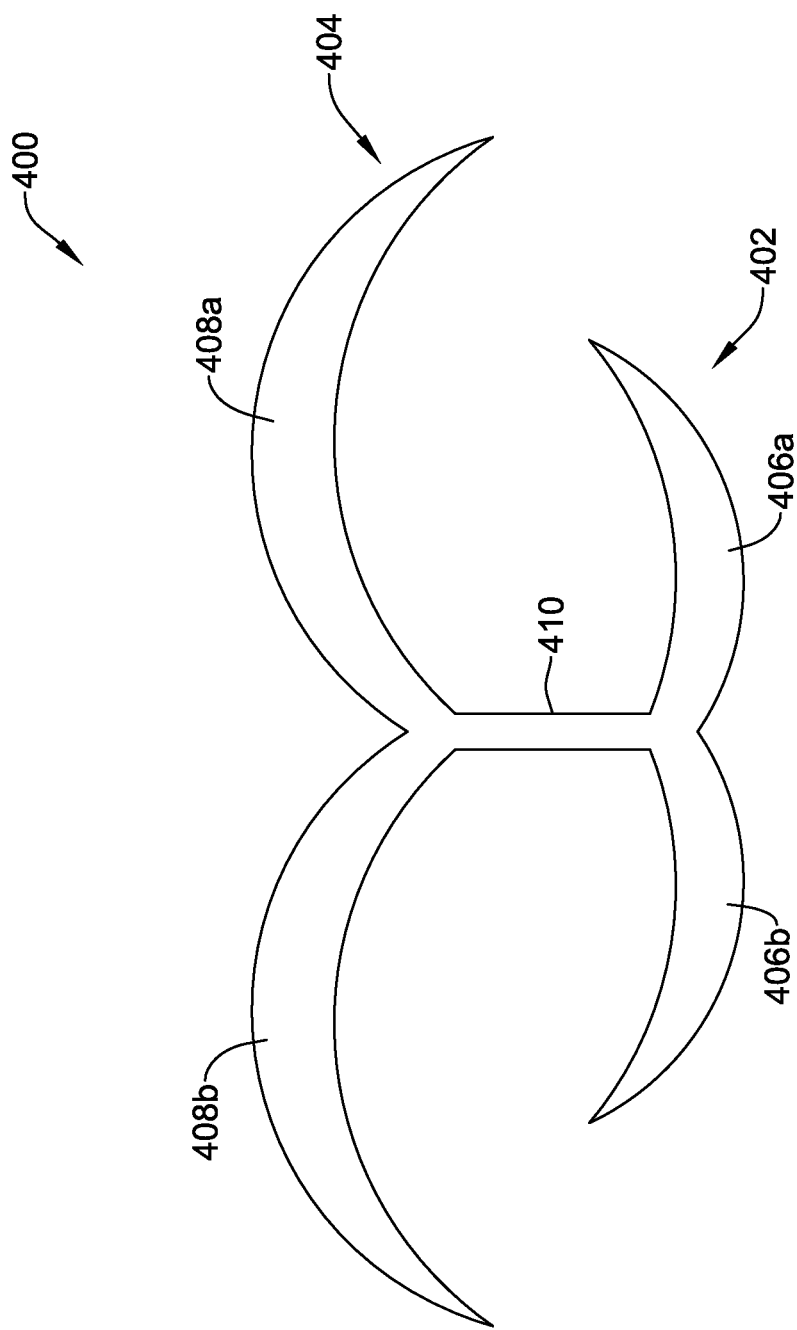
FIG. 7 is a side view of another illustrative radiopaque anchor.

FIG. 7 is a perspective view of an illustrative implantable radiopaque marker or anchor 400. The radiopaque anchor 400 is configured to be implanted in the nadir (hinge point) of the non-coronary, right coronary, and/or left-coronary cusps to serve as markers for identification of the proper plane for valve deployment. However, the radiopaque anchor 400 may be used in other anatomical locations for different procedures, as desired. The radiopaque anchor 400 may have dimensions in the range of about 0.5 millimeters (mm) to about 2.0 mm, about 0.75 mm to about 1.75 mm, or about 1.0 to about 1.5 mm. In some cases, the radiopaque anchor 400 may have dimensions of less than 0.5 mm or greater than 2.0 mm, as desired. It is contemplated that the size of the radiopaque anchor 400 may be determined based on the anatomical location it will be implanted.

The radiopaque anchor 400 has a proximal end region 402, a distal end region 404, and an intermediate region 410 extending between the proximal end region 402 and the distal end region 404. The radiopaque anchor 400 may be formed from a shape memory or superelastic material, such as, but not limited to, nitinol. The radiopaque anchor 400 may be coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 400 may be made radiopaque. Other materials and/or techniques may be used as desired. The proximal end region 402 includes one or more hooks or tines 406a, 406b (collectively, 406). Similarly, the distal end region 404 includes one or more hooks or tines 408a, 408b (collectively, 408). The radiopaque anchor 400 may be formed such that the tines 406, 408 extend radially outward from the intermediate region 406 when the radiopaque anchor 400 is in the "remembered" or preformed shape. A biasing force (such as a deployment tube) may bias the tines 406, 408 such that they extend generally parallel to a longitudinal axis of the intermediate region 410. Once the biasing force is removed the tines 406, 408 return to their curved talon-like shape.

Figure 8:
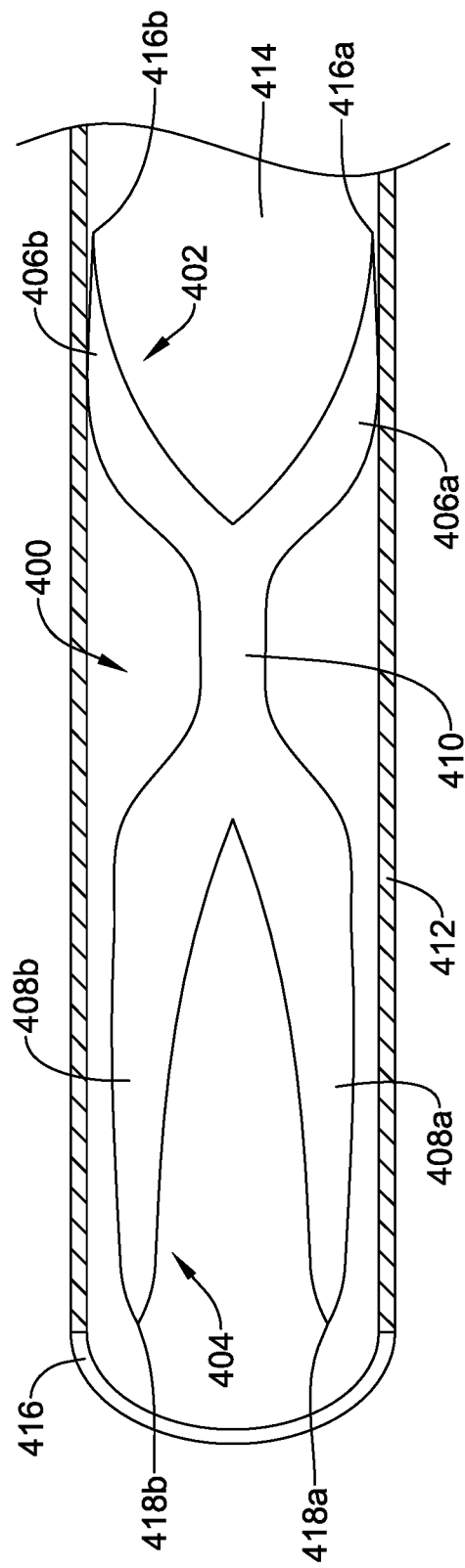
FIG. 8 is a partial cross-sectional view of the illustrative radiopaque anchor of FIG. 7 disposed within a delivery tube.

FIG. 8 illustrates a partial cross-sectional view of the illustrative radiopaque anchor 400 disposed within a delivery tube 412. It is contemplated that the delivery tube 412 may be a part of a pigtail catheter, a part of another delivery device, or a separate tubular component disposed within the lumen of a pigtail catheter or other delivery device. The tines 406, 408 of the radiopaque anchor 400 are deflected such that they extend generally parallel to the longitudinal axis of the intermediate region 410. This may both reduce the overall profile of the radiopaque anchor 400 for delivery and facilitate deployment into the tissue. A delivery tube or push member (not explicitly shown) may be slidably disposed within the lumen 414 of the delivery tube 412. The delivery tube 412 may be delivered to the desired treatment location using an outer sheath and radiopaque fluid and/or contrast agent in a similar manner to that described herein. Once the distal end 416 of the delivery tube 412 is adjacent to the target location, a push member may be used to exert a distal force on the proximal ends 416a, 416b (collectively, 416) of the proximal tines 406. The distal ends 418a, 418b (collectively, 418) of the distal tines 408 may be pointed or sharp to puncture or penetrate the tissue as it is deployed. As the radiopaque anchor 400 is deployed, the tines 406, 408 resume their curved (or remembered) shape. The curved shape of the tines 406, 408 in the deployed configuration (e.g., FIG. 7) captures or grips the tissue to ensure the radiopaque anchor 400 does not dislodge from the tissue.

Figure 9:
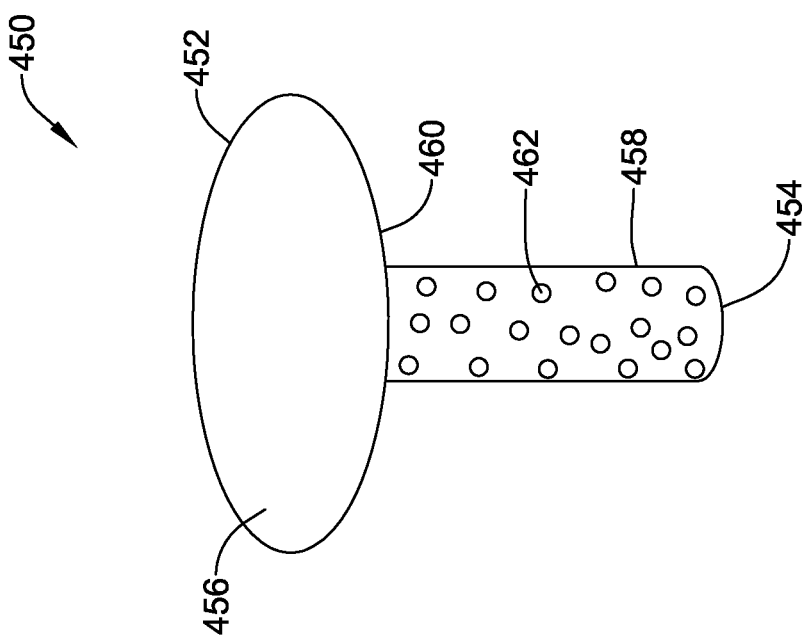
FIGS. 9-15 are perspective views of other illustrative radiopaque anchors.

FIG. 9 is a side view of another illustrative implantable radiopaque marker or anchor 450. The radiopaque anchor 450 is configured to be implanted in the nadir (hinge point) of the non-coronary, right coronary, and/or left-coronary cusps to serve as markers for identification of the proper plane for valve deployment. However, the radiopaque anchor 450 may be used in other anatomical locations for different procedures, as desired. The radiopaque anchor 450 may have dimensions in the range of about 0.5 millimeters (mm) to about 2.0 mm, about 0.75 mm to about 1.75 mm, or about 1.0 to about 1.5 mm. In some cases, the radiopaque anchor 450 may have dimensions of less than 0.5 mm or greater than 2.0 mm, as desired. It is contemplated that the size of the radiopaque anchor 450 may be determined based on the anatomical location it will be implanted.

The radiopaque anchor 450 extends from a proximal end 452 to a distal end 454. The proximal end region 456, adjacent to the proximal end 452, may have a flattened spheroid shape. However, other shapes may be used as desired. In some cases, the flattened spheroid shape (or other enlarged shape) may be omitted such that the radiopaque anchor 450 has a generally uniform shape from the proximal end 452 to the distal end 454 thereof. The proximal end region 456 may be configured to provide a surface for actuating the radiopaque anchor 450 through a lumen during deployment, limit penetration of the radiopaque anchor 450 into the tissue, and/or seal the puncture in the tissue caused by deployment of the radiopaque anchor 450. A cylindrical elongate member 458 may extend distally from the distal end 460 of the proximal end region 456 to the distal end 454 of the radiopaque anchor 450. In some cases, the elongate member 458 may be a generally solid component. In other cases, the elongate member 458 may be a hollow component defining a central cavity therein (not explicitly shown). In some embodiments, the distal end 454 of the radiopaque anchor 450 may be pointed to facilitate deployment of the radiopaque anchor 450 into the tissue.

The radiopaque anchor 450 may be formed from a biodegradable or bioabsorbable polymer such as, but not limited to, polylactic acid (PLA), polyglycolic acid (PGA), polycaprolactone (PCL), polycarbonate, polydioxanone (PDO), trimethylene carbonate (TMC), and/or copolymers made from these monomers. The radiopaque anchor 450 may be made radiopaque by including doping, coating the biodegradable polymer with, or otherwise including, with radiopaque materials, shown schematically at 462, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). It is further contemplated that the radiopaque particles may be disposed within a cavity of the radiopaque anchor 450, such as, but not limited, within the elongate member 458. These are just some examples of how the radiopaque anchor 450 may be made radiopaque. Other materials and/or techniques may be used as desired.

Figure 10:
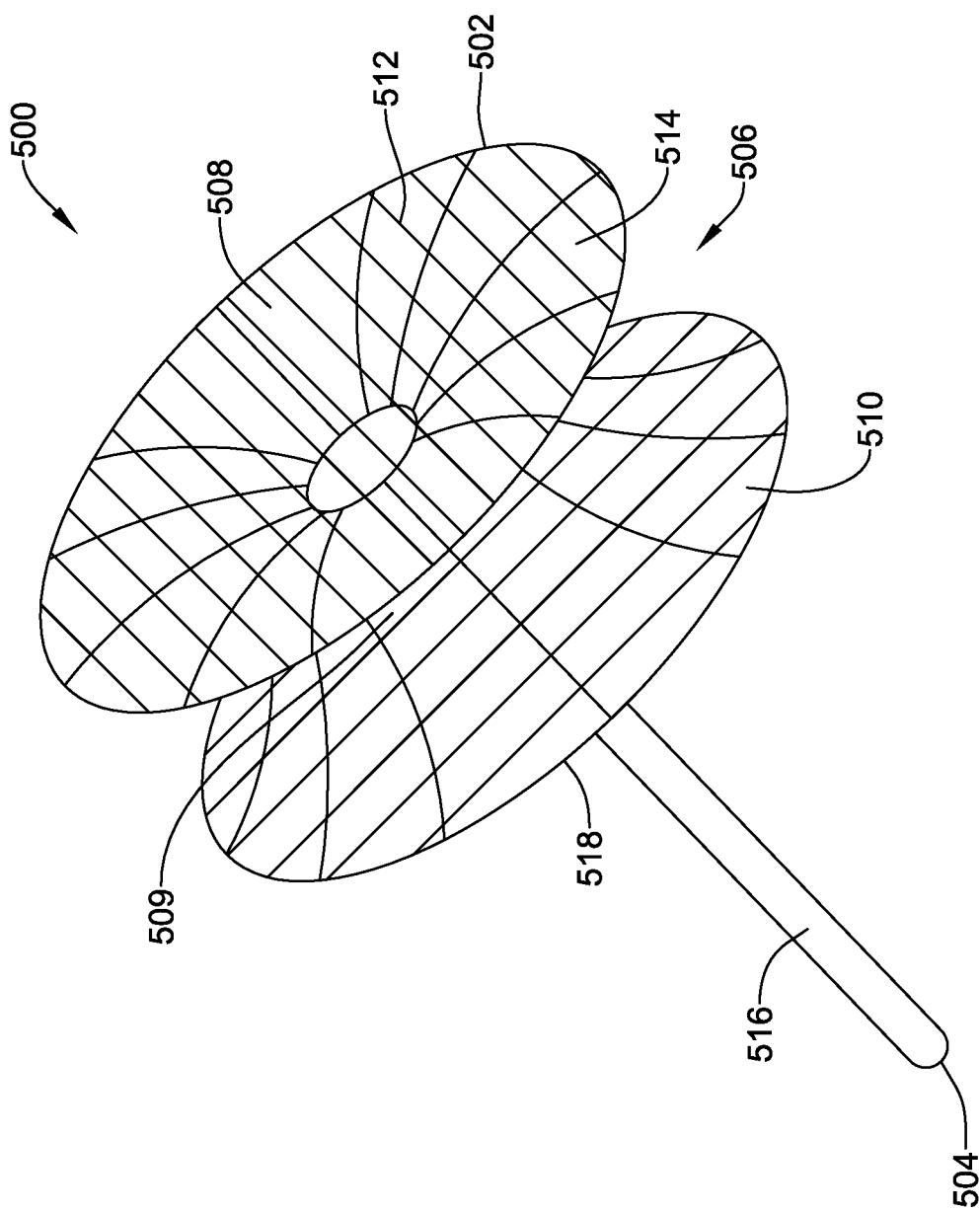

FIG. 10 is a perspective view of another illustrative implantable radiopaque marker or anchor 500. The radiopaque anchor 500 is configured to be implanted in the nadir (hinge point) of the non-coronary, right coronary, and/or left-coronary cusps to serve as markers for identification of the proper plane for valve deployment. However, the radiopaque anchor 500 may be used in other anatomical locations for different procedures, as desired. The radiopaque anchor 500 may have dimensions in the range of about 0.5 millimeters (mm) to about 2.0 mm, about 0.75 mm to about 1.75 mm, or about 1.0 to about 1.5 mm. In some cases, the radiopaque anchor 500 may have dimensions of less than 0.5 mm or greater than 2.0 mm, as desired. It is contemplated that the size of the radiopaque anchor 500 may be determined based on the anatomical location it will be implanted.

The radiopaque anchor 500 extends from a proximal end 502 to a distal end 504. The proximal end region 506, adjacent to the proximal end 502, may have a flared cylindrical shape. For example, a first end region 508 and a second end region 510 may have a larger radial dimension than an intermediate region 509. However, other shapes may be used as desired. The proximal end region 506 may have a woven structure fabricated from a number of filaments or struts 512. In some embodiments, the proximal end region 506 may be knitted or braided with a single filament or strut interwoven with itself and defining open cells 514. In other embodiments, the proximal end region 506 may be braided with several filaments or struts interwoven together and defining open cells 514. In yet other embodiments, the proximal end region 506 may be laser cut to define the openings 514. At least the proximal end region 506 of the radiopaque anchor 500 may be formed from a shape memory or superelastic material, such as, but not limited to, nitinol, so that the proximal end region 506 is self-expanding upon deployment. During navigation to the deployment location, the proximal end region 506 may be radially compressed to a lower profile delivery configuration. It is contemplated that the proximal end region 506 may be formed from other expandable structures, as desired.

The proximal end region 506 may be configured to provide a surface for actuating the radiopaque anchor 500 through a lumen during deployment, limit penetration of the radiopaque anchor 500 into the tissue, and/or seal the puncture in the tissue caused by deployment of the radiopaque anchor 500. A cylindrical elongate member 516 may extend distally from the distal end 518 of the proximal end region 506 to the distal end 504 of the radiopaque anchor 500. In some cases, the elongate member 516 may be a generally solid component. In other cases, the elongate member 516 may be a hollow component defining a central cavity therein (not explicitly shown) which may be filed with a radiopaque material. In some embodiments, the distal end 504 of the radiopaque anchor 500 may be pointed to facilitate deployment of the radiopaque anchor 500 into the tissue.

The radiopaque anchor 500, or components thereof, may be formed from, coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 500 may be made radiopaque. Other materials and/or techniques may be used as desired.

Figure 11:
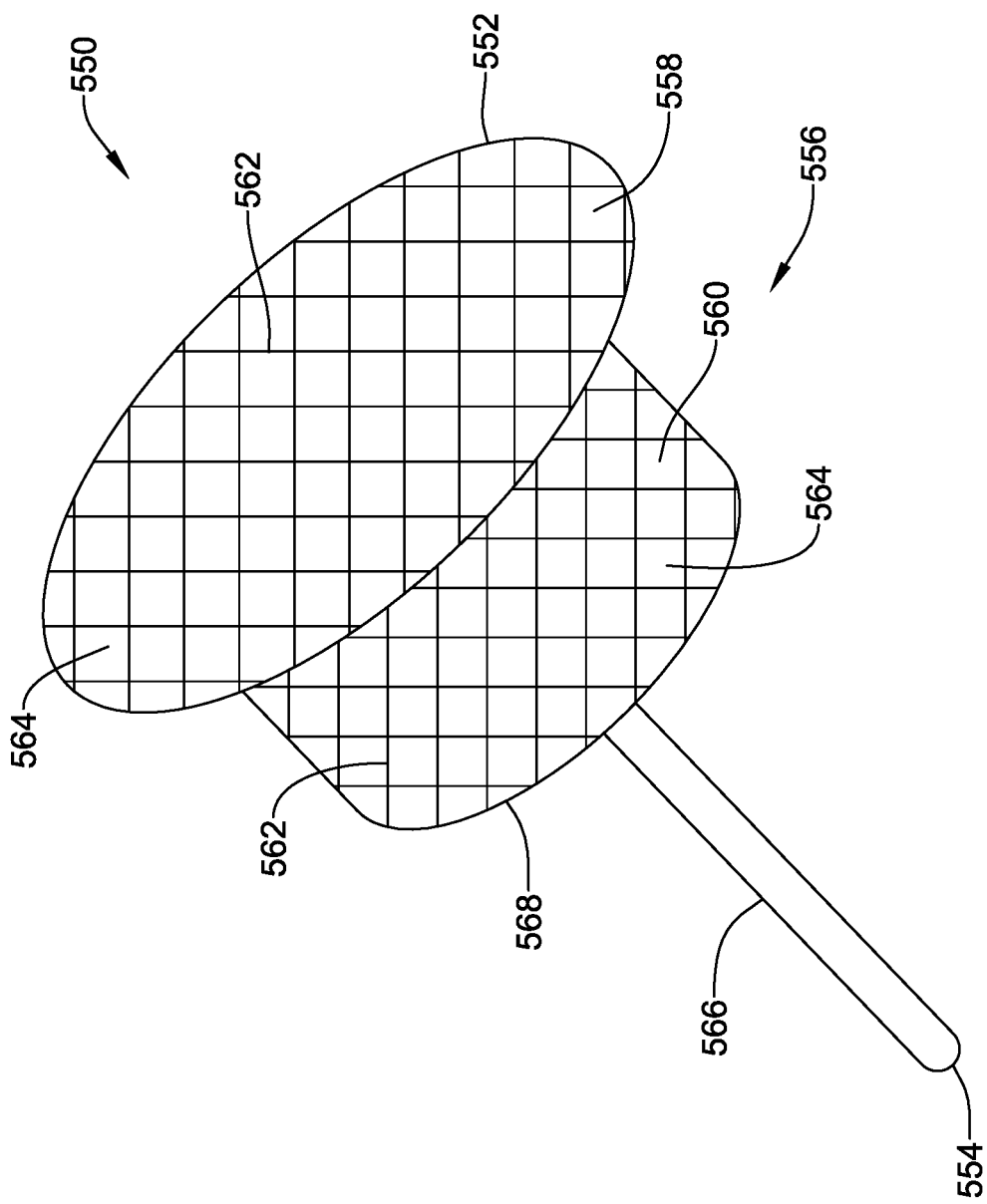

FIG. 11 is a perspective view of another illustrative implantable radiopaque marker or anchor 550. The radiopaque anchor 550 is configured to be implanted in the nadir (hinge point) of the non-coronary, right coronary, and/or left-coronary cusps to serve as markers for identification of the proper plane for valve deployment. However, the radiopaque anchor 550 may be used in other anatomical locations for different procedures, as desired. The radiopaque anchor 550 may have dimensions in the range of about 0.5 millimeters (mm) to about 2.0 mm, about 0.75 mm to about 1.75 mm, or about 1.0 to about 1.5 mm. In some cases, the radiopaque anchor 550 may have dimensions of less than 0.5 mm or greater than 2.0 mm, as desired. It is contemplated that the size of the radiopaque anchor 550 may be determined based on the anatomical location it will be implanted.

The radiopaque anchor 550 extends from a proximal end 552 to a distal end 554. The proximal end region 556, adjacent to the proximal end 552, may have a flared cylindrical shape. For example, a first end region 558 may have a larger radial dimension than a second end region 560. However, other shapes may be used as desired. The proximal end region 556 may have a woven structure fabricated from a number of filaments or struts 562. In some embodiments, the proximal end region 556 may be knitted or braided with a single filament or strut interwoven with itself and defining open cells 564. In other embodiments, the proximal end region 556 may be braided with several filaments or struts interwoven together and defining open cells 564. In yet other embodiments, the proximal end region 556 may be laser cut to define the openings 564. At least the proximal end region 556 of the radiopaque anchor 550 may be formed from a shape memory or superelastic material, such as, but not limited to, nitinol, so that the proximal end region 556 is self-expanding upon deployment. During navigation to the deployment location, the proximal end region 556 may be radially compressed to a lower profile delivery configuration. It is contemplated that the proximal end region 556 may be formed from other expandable structures, as desired.

The proximal end region 556 may be configured to provide a surface for actuating the radiopaque anchor 550 through a lumen during deployment, limit penetration of the radiopaque anchor 550 into the tissue, and/or seal the puncture in the tissue caused by deployment of the radiopaque anchor 550. A cylindrical elongate member 566 may extend distally from the distal end 568 of the proximal end region 556 to the distal end 554 of the radiopaque anchor 550. In some cases, the elongate member 566 may be a generally solid component. In other cases, the elongate member 566 may be a hollow component defining a central cavity therein (not explicitly shown) which may be filed with a radiopaque material. In some embodiments, the distal end 554 of the radiopaque anchor 550 may be pointed to facilitate deployment of the radiopaque anchor 550 into the tissue.

The radiopaque anchor 550, or components thereof, may be formed from, coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 550 may be made radiopaque. Other materials and/or techniques may be used as desired.

Figure 12:
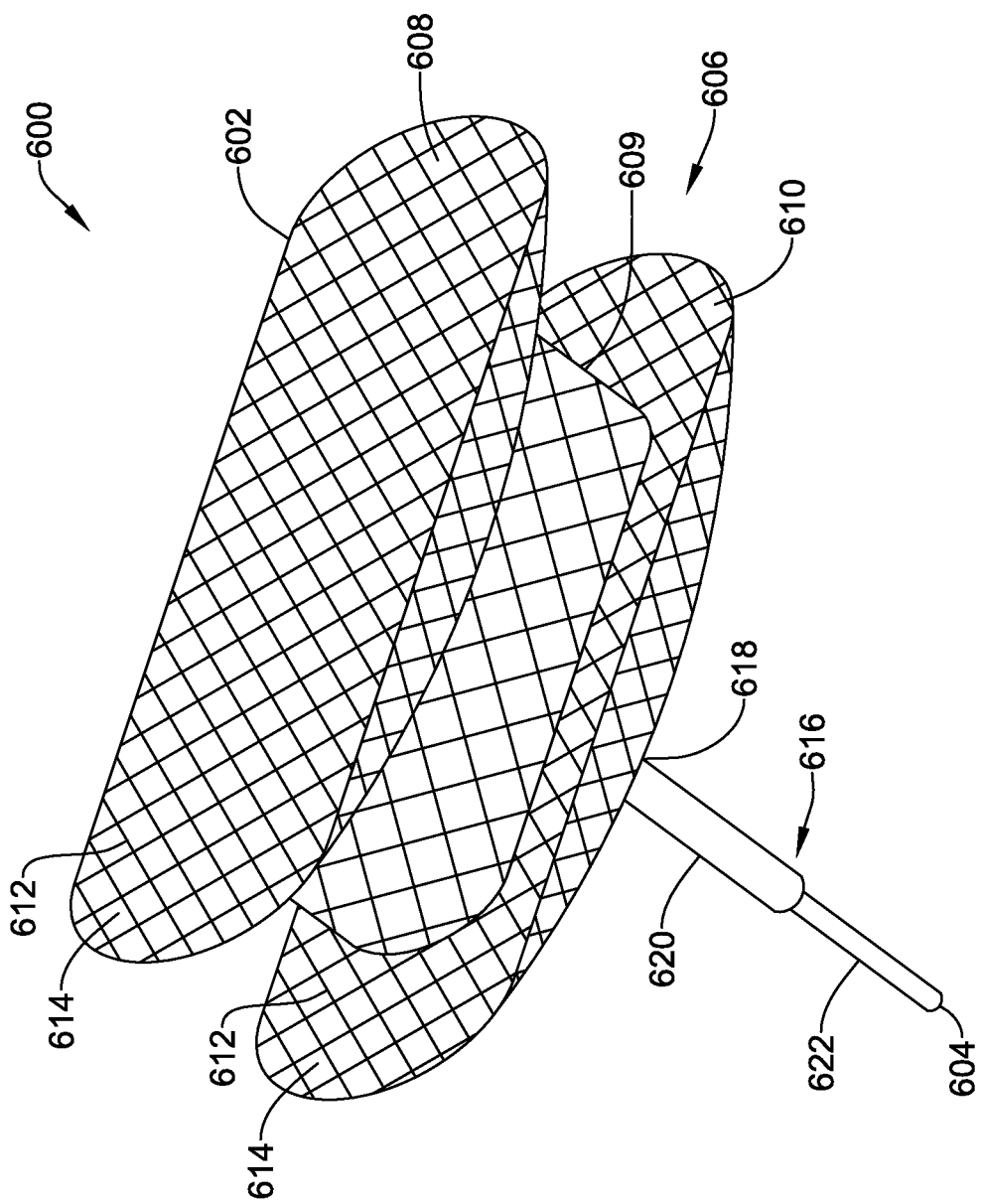

FIG. 12 is a perspective view of another illustrative implantable radiopaque marker or anchor 600. The radiopaque anchor 600 is configured to be implanted in the nadir (hinge point) of the non-coronary, right coronary, and/or left-coronary cusps to serve as markers for identification of the proper plane for valve deployment. However, the radiopaque anchor 600 may be used in other anatomical locations for different procedures, as desired. The radiopaque anchor 600 may have dimensions in the range of about 0.5 millimeters (mm) to about 2.0 mm, about 0.75 mm to about 1.75 mm, or about 1.0 to about 1.5 mm. In some cases, the radiopaque anchor 600 may have dimensions of less than 0.5 mm or greater than 2.0 mm, as desired. It is contemplated that the size of the radiopaque anchor 600 may be determined based on the anatomical location it will be implanted.

The radiopaque anchor 600 extends from a proximal end 602 to a distal end 604. The proximal end region 606, adjacent to the proximal end 602, may have a generally ellipsoid cross-sectional shape, or a rectangular shape with at least two opposing edges having curved surfaces. The proximal end region 606 may be flared such that a first end region 608 and a second end region 610 may have a larger radial dimension than an intermediate region 609 disposed therebetween. However, other shapes may be used as desired. The proximal end region 606 may have a woven structure fabricated from a number of filaments or struts 612. In some embodiments, the proximal end region 606 may be knitted or braided with a single filament or strut interwoven with itself and defining open cells 614. In other embodiments, the proximal end region 606 may be braided with several filaments or struts interwoven together and defining open cells 614. In yet other embodiments, the proximal end region 606 may be laser cut to define the openings 614. At least the proximal end region 606 of the radiopaque anchor 600 may be formed from a shape memory or superelastic material, such as, but not limited to, nitinol, so that the proximal end region 606 is self-expanding upon deployment. During navigation to the deployment location, the proximal end region 606 may be radially compressed to a lower profile delivery configuration. It is contemplated that the proximal end region 606 may be formed from other expandable structures, as desired.

The proximal end region 606 may be configured to provide a surface for actuating the radiopaque anchor 600 through a lumen during deployment, limit penetration of the radiopaque anchor 600 into the tissue, and/or seal the puncture in the tissue caused by deployment of the radiopaque anchor 600. A cylindrical elongate member 616 may extend distally from the distal end 618 of the proximal end region 606 to the distal end 604 of the radiopaque anchor 600. In some cases, the elongate member 616 may be a generally solid component. In other cases, the elongate member 616 may be a hollow component defining a central cavity therein (not explicitly shown) which may be filed with a radiopaque material. In some embodiments, the distal end 604 of the radiopaque anchor 600 may be pointed to facilitate deployment of the radiopaque anchor 600 into the tissue. It is further contemplated that the cross-sectional dimension may vary along the length of the elongate member 616 to facilitate deployment. For example, a distal end region 622 may have a smaller cross-sectional dimension than a proximal end region 620 of the elongate member 616. This is just one example.

The radiopaque anchor 600, or components thereof, may be formed from, coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 600 may be made radiopaque. Other materials and/or techniques may be used as desired.

Figure 13:
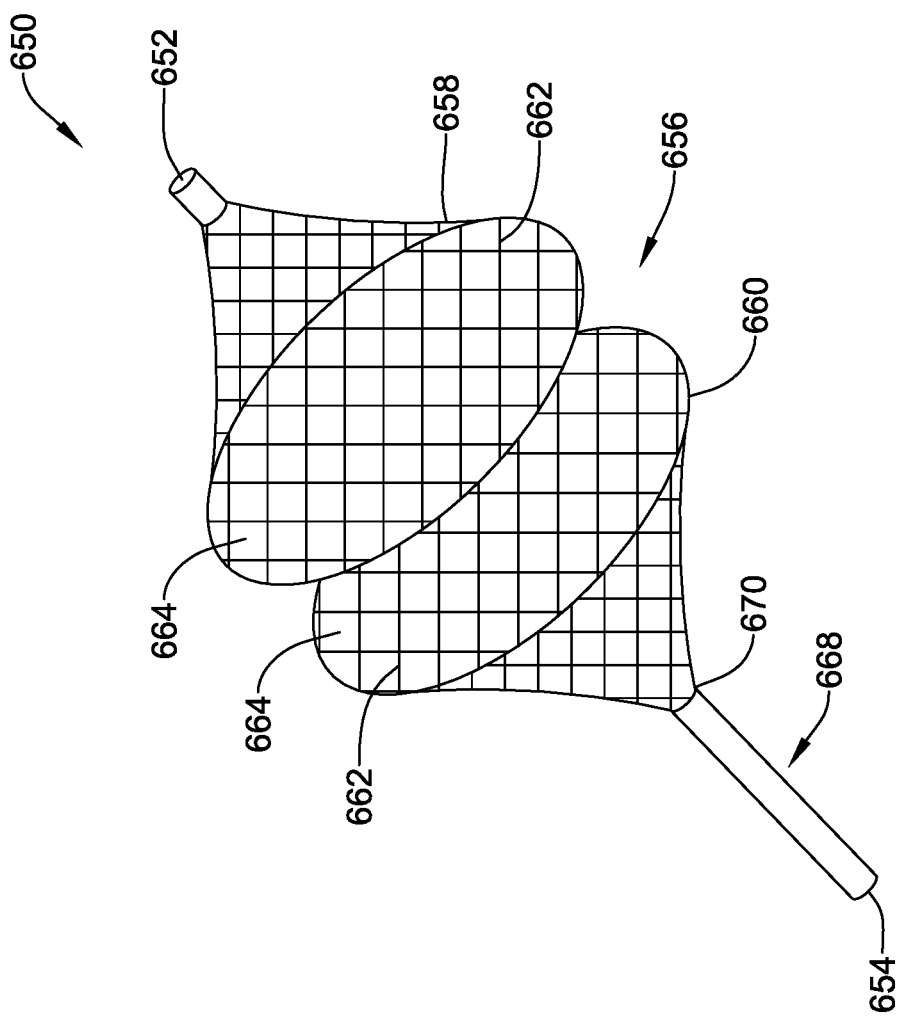

FIG. 13 is a perspective view of another illustrative implantable radiopaque marker or anchor 650. The radiopaque anchor 650 is configured to be implanted in the nadir (hinge point) of the non-coronary, right coronary, and/or left-coronary cusps to serve as markers for identification of the proper plane for valve deployment. However, the radiopaque anchor 650 may be used in other anatomical locations for different procedures, as desired. The radiopaque anchor 650 may have dimensions in the range of about 0.5 millimeters (mm) to about 2.0 mm, about 0.75 mm to about 1.75 mm, or about 1.0 to about 1.5 mm. In some cases, the radiopaque anchor 650 may have dimensions of less than 0.5 mm or greater than 2.0 mm, as desired. It is contemplated that the size of the radiopaque anchor 650 may be determined based on the anatomical location it will be implanted.

The radiopaque anchor 650 extends from a proximal end 652 to a distal end 654. The proximal end region 656, adjacent to the proximal end 652, may have a first end region 658 and a second end region 660. The first end region 658 may have a three-dimensional tear drop shape that tapers or decreases in cross-sectional dimension in the proximal direction (e.g., towards the proximal end 652). The second end region 660 may have a three-dimensional tear drop shape that tapers or decreases in cross-sectional dimension in the distal direction (e.g., towards the distal end 654). However, other shapes may be used as desired. The proximal end region 656 may have a woven structure fabricated from a number of filaments or struts 662. In some embodiments, the proximal end region 656 may be knitted or braided with a single filament or strut interwoven with itself and defining open cells 664. In other embodiments, the proximal end region 656 may be braided with several filaments or struts interwoven together and defining open cells 664. In yet other embodiments, the proximal end region 656 may be laser cut to define the openings 664. At least the proximal end region 656 of the radiopaque anchor 650 may be formed from a shape memory or superelastic material, such as, but not limited to, nitinol, so that the proximal end region 656 is self-expanding upon deployment. During navigation to the deployment location, the proximal end region 656 may be radially compressed to a lower profile delivery configuration. It is contemplated that the proximal end region 656 may be formed from other expandable structures, as desired.

The proximal end region 656 may be configured to provide a surface for actuating the radiopaque anchor 650 through a lumen during deployment, limit penetration of the radiopaque anchor 650 into the tissue, and/or seal the puncture in the tissue caused by deployment of the radiopaque anchor 650. A cylindrical elongate member 668 may extend distally from the distal end 670 of the proximal end region 656 to the distal end 654 of the radiopaque anchor 650. In some cases, the elongate member 668 may be a generally solid component. In other cases, the elongate member 668 may be a hollow component defining a central cavity therein (not explicitly shown) which may be filed with a radiopaque material. In some embodiments, the distal end 654 of the radiopaque anchor 650 may be pointed to facilitate deployment of the radiopaque anchor 650 into the tissue. It is further contemplated that the cross-sectional dimension may vary along the length of the elongate member 668 to facilitate deployment.

The radiopaque anchor 650, or components thereof, may be formed from, coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 650 may be made radiopaque. Other materials and/or techniques may be used as desired.

Figure 14:
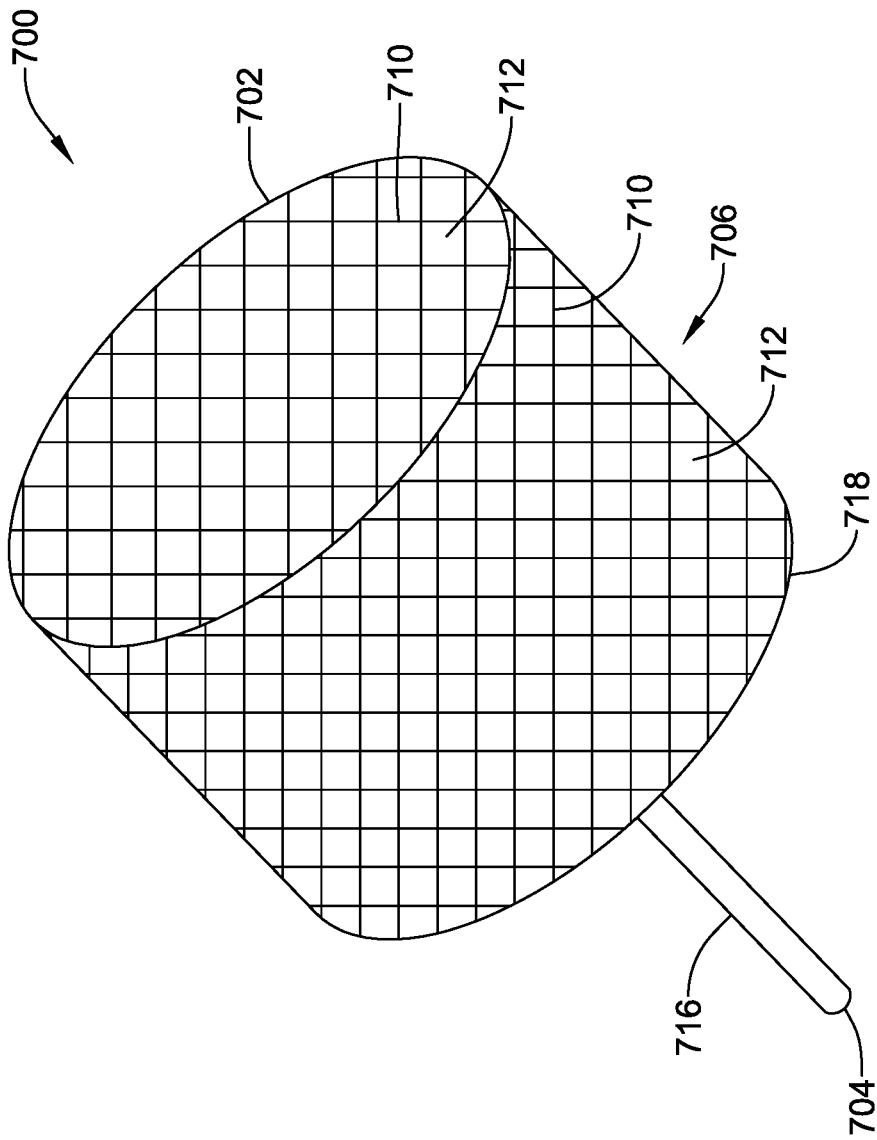

FIG. 14 is a perspective view of another illustrative implantable radiopaque marker or anchor 700. The radiopaque anchor 700 is configured to be implanted in the nadir (hinge point) of the non-coronary, right coronary, and/or left-coronary cusps to serve as markers for identification of the proper plane for valve deployment. However, the radiopaque anchor 700 may be used in other anatomical locations for different procedures, as desired. The radiopaque anchor 700 may have dimensions in the range of about 0.5 millimeters (mm) to about 2.0 mm, about 0.75 mm to about 1.75 mm, or about 1.0 to about 1.5 mm. In some cases, the radiopaque anchor 700 may have dimensions of less than 0.5 mm or greater than 2.0 mm, as desired. It is contemplated that the size of the radiopaque anchor 700 may be determined based on the anatomical location it will be implanted.

The radiopaque anchor 700 extends from a proximal end 702 to a distal end 704. The proximal end region 706, adjacent to the proximal end 702, may have a generally cylindrical shape having a generally uniform cross-sectional dimension along a length thereof. However, other shapes may be used as desired. The proximal end region 706 may have a woven structure fabricated from a number of filaments or struts 710. In some embodiments, the proximal end region 706 may be knitted or braided with a single filament or strut interwoven with itself and defining open cells 712. In other embodiments, the proximal end region 706 may be braided with several filaments or struts interwoven together and defining open cells 712. In yet other embodiments, the proximal end region 706 may be laser cut to define the openings 712. At least the proximal end region 706 of the radiopaque anchor 700 may be formed from a shape memory or superelastic material, such as, but not limited to, nitinol, so that the proximal end region 706 is self-expanding upon deployment. During navigation to the deployment location, the proximal end region 706 may be radially compressed to a lower profile delivery configuration. It is contemplated that the proximal end region 706 may be formed from other expandable structures, as desired.

The proximal end region 706 may be configured to provide a surface for actuating the radiopaque anchor 700 through a lumen during deployment, limit penetration of the radiopaque anchor 700 into the tissue, and/or seal the puncture in the tissue caused by deployment of the radiopaque anchor 700. A cylindrical elongate member 716 may extend distally from the distal end 718 of the proximal end region 706 to the distal end 704 of the radiopaque anchor 700. In some cases, the elongate member 716 may be a generally solid component. In other cases, the elongate member 716 may be a hollow component defining a central cavity therein (not explicitly shown) which may be filed with a radiopaque material. In some embodiments, the distal end 704 of the radiopaque anchor 700 may be pointed to facilitate deployment of the radiopaque anchor 700 into the tissue. It is further contemplated that the cross-sectional dimension may vary along the length of the elongate member 716 to facilitate deployment.

The radiopaque anchor 700, or components thereof, may be formed from, coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 700 may be made radiopaque. Other materials and/or techniques may be used as desired.

Figure 15:
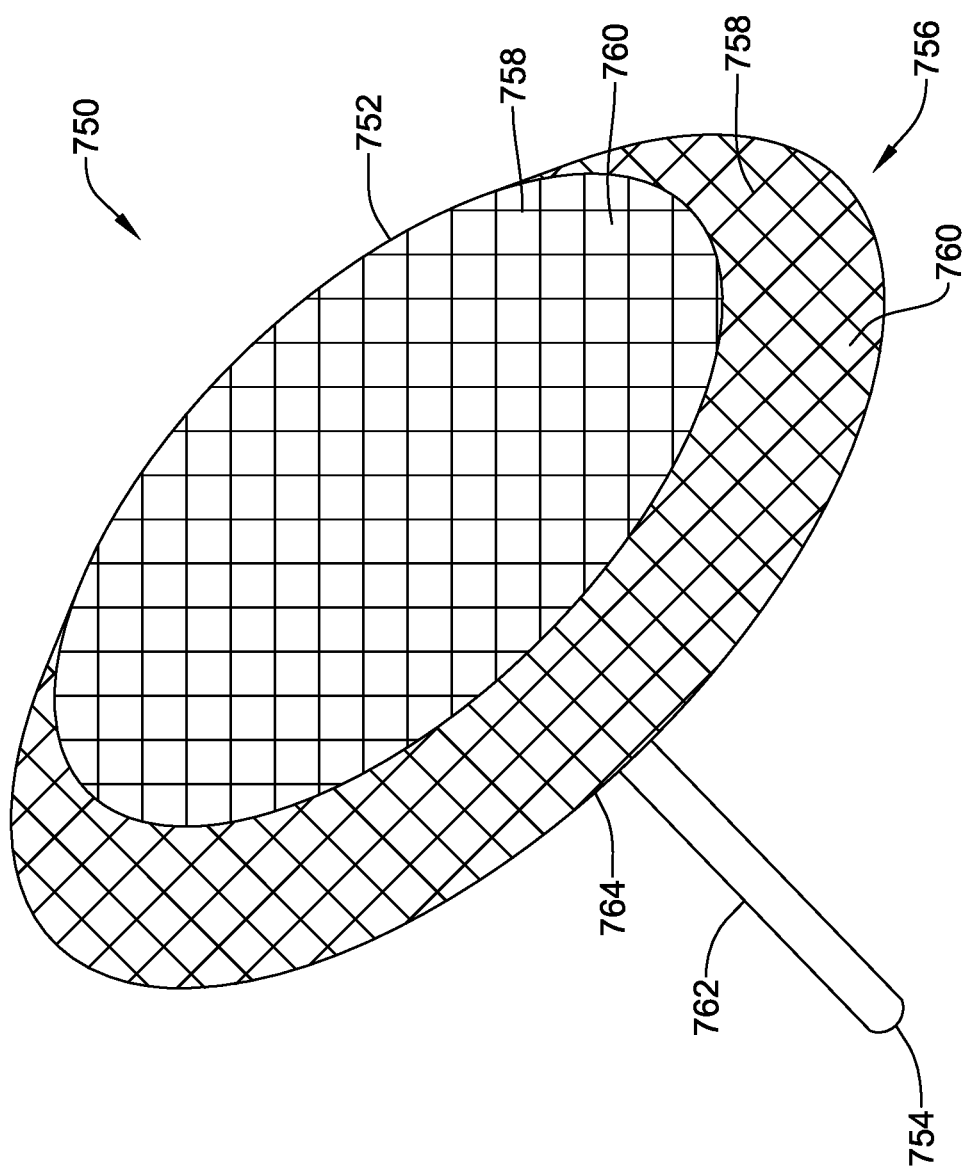

FIG. 15 is a perspective view of another illustrative implantable radiopaque marker or anchor 750. The radiopaque anchor 750 is configured to be implanted in the nadir (hinge point) of the non-coronary, right coronary, and/or left-coronary cusps to serve as markers for identification of the proper plane for valve deployment. However, the radiopaque anchor 750 may be used in other anatomical locations for different procedures, as desired. The radiopaque anchor 750 may have dimensions in the range of about 0.5 millimeters (mm) to about 2.0 mm, about 0.75 mm to about 1.75 mm, or about 1.0 to about 1.5 mm. In some cases, the radiopaque anchor 750 may have dimensions of less than 0.5 mm or greater than 2.0 mm, as desired. It is contemplated that the size of the radiopaque anchor 750 may be determined based on the anatomical location it will be implanted.

The radiopaque anchor 750 extends from a proximal end 752 to a distal end 754. The proximal end region 756, adjacent to the proximal end 752, may have a generally flattened spheroid shape. However, other shapes may be used as desired. The proximal end region 756 may have a woven structure fabricated from a number of filaments or struts 758. In some embodiments, the proximal end region 756 may be knitted or braided with a single filament or strut interwoven with itself and defining open cells 760. In other embodiments, the proximal end region 756 may be braided with several filaments or struts interwoven together and defining open cells 760. In yet other embodiments, the proximal end region 756 may be laser cut to define the openings 760. At least the proximal end region 756 of the radiopaque anchor 750 may be formed from a shape memory or superelastic material, such as, but not limited to, nitinol, so that the proximal end region 756 is self-expanding upon deployment. During navigation to the deployment location, the proximal end region 756 may be radially compressed to a lower profile delivery configuration. It is contemplated that the proximal end region 756 may be formed from other expandable structures, as desired.

The proximal end region 756 may be configured to provide a surface for actuating the radiopaque anchor 750 through a lumen during deployment, limit penetration of the radiopaque anchor 750 into the tissue, and/or seal the puncture in the tissue caused by deployment of the radiopaque anchor 750. A cylindrical elongate member 762 may extend distally from the distal end 764 of the proximal end region 756 to the distal end 754 of the radiopaque anchor 750. In some cases, the elongate member 762 may be a generally solid component. In other cases, the elongate member 762 may be a hollow component defining a central cavity therein (not explicitly shown) which may be filed with a radiopaque material. In some embodiments, the distal end 754 of the radiopaque anchor 750 may be pointed to facilitate deployment of the radiopaque anchor 750 into the tissue. It is further contemplated that the cross-sectional dimension may vary along the length of the elongate member 762 to facilitate deployment.

The radiopaque anchor 750, or components thereof, may be formed from, coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 750 may be made radiopaque. Other materials and/or techniques may be used as desired.

Figure 16:
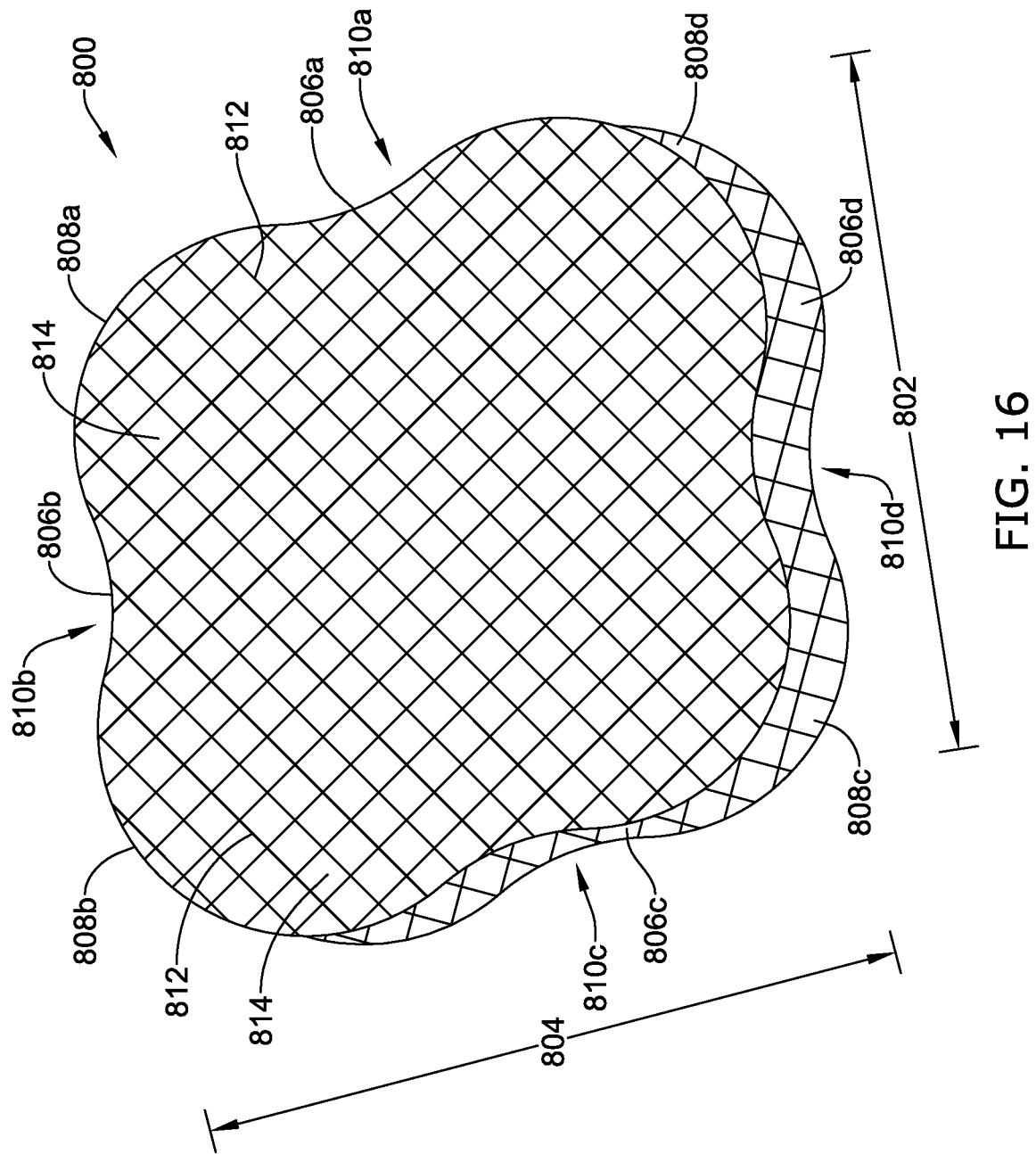
FIGS. 16-17 are perspective views of alternative structures for portions of radiopaque anchors.

FIG. 16 is a perspective view of another illustrative proximal end region 800 of a radiopaque anchor that may be used in addition to or in place of any of the structures described herein. The proximal end region 800 may have a generally equal length 802 and width 804. The edges 806a, 806b, 806c, 806d (collectively, 806) of the proximal end region 800 may be curved to form rounded corners 808a, 808b, 808c, 808d (collectively, 808) and radially inward extending valleys 810a, 810b, 810c, 810d (collectively, 810). The proximal end region 800 may have a woven structure fabricated from a number of filaments or struts 812. In some embodiments, the proximal end region 800 may be knitted or braided with a single filament or strut interwoven with itself and defining open cells 814. In other embodiments, the proximal end region 800 may be braided with several filaments or struts interwoven together and defining open cells 814. In yet other embodiments, the proximal end region 800 may be laser cut to define the openings 814. At least the proximal end region 800 may be formed from a shape memory or superelastic material, such as, but not limited to, nitinol, so that the proximal end region 800 is self-expanding upon deployment. During navigation to the deployment location, the proximal end region 800 may be radially compressed to a lower profile delivery configuration. It is contemplated that the proximal end region 800 may be formed from other expandable structures, as desired.

Figure 17:
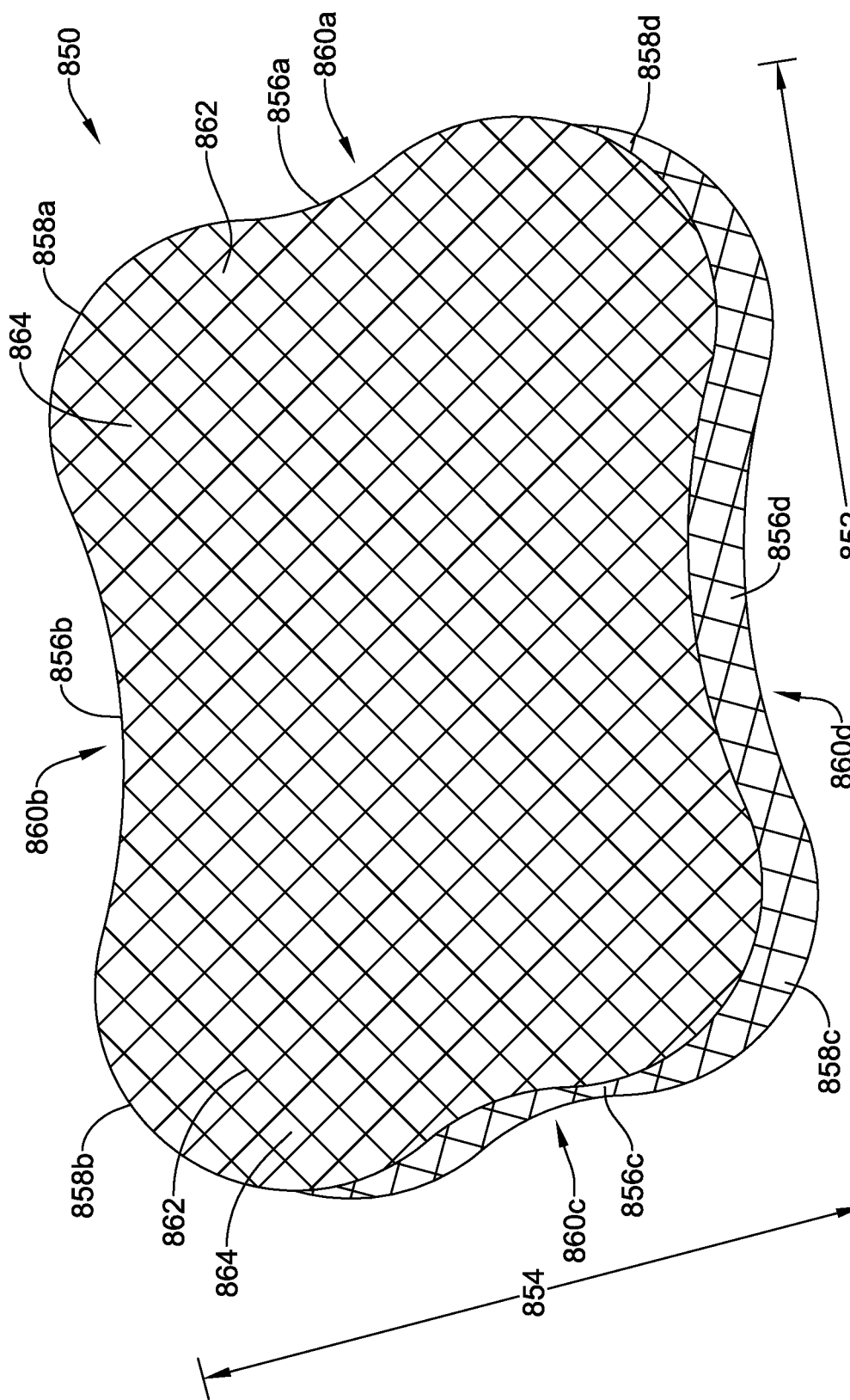

FIG. 17 is a perspective view of another illustrative proximal end region 850 of a radiopaque anchor that may be used in addition to or in place of any of the structures described herein. The proximal end region 850 may have a length 852 that is greater than a width 854 thereof. The reverse configuration is also contemplated. The edges 856*a*, 856*b*, 856*c*, 856*d* (collectively, 856) of the proximal end region 850 may be curved to form rounded corners 858*a*, 858*b*, 858*c*, 858*d* (collectively, 858) and radially inward extending valleys 860*a*, 860*b*, 860*c*, 860*d* (collectively, 860). The proximal end region 850 may have a woven structure fabricated from a number of filaments or struts 862. In some embodiments, the proximal end region 850 may be knitted or braided with a single filament or strut interwoven with itself and defining open cells 864. In other embodiments, the proximal end region 850 may be braided with several filaments or struts interwoven together and defining open cells 864. In yet other embodiments, the proximal end region 850 may be laser cut to define the openings 864. At least the proximal end region 850 may be formed from a shape memory or superelastic material, such as, but not limited to, nitinol, so that the proximal end region 850 is self-expanding upon deployment. During navigation to the deployment location, the proximal end region 850 may be radially compressed to a lower profile delivery configuration. It is contemplated that the proximal end region 850 may be formed from other expandable structures, as desired.

Figure 18:
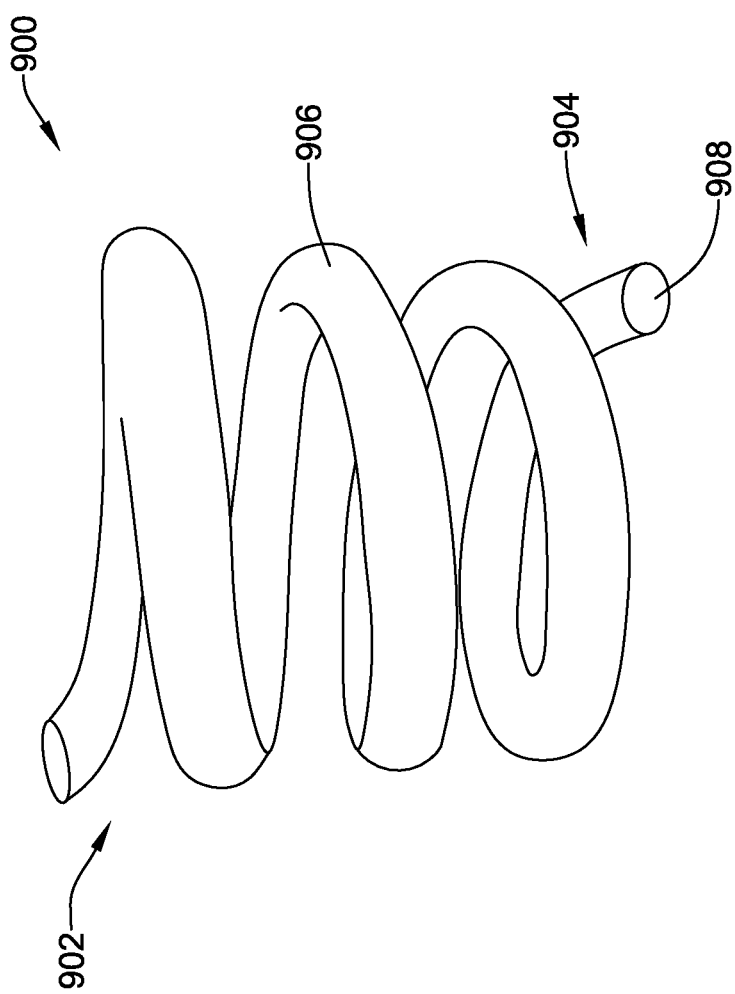
FIG. 18 is a perspective view of another illustrative radiopaque anchor.

FIG. 18 is a perspective view of an illustrative implantable radiopaque marker or anchor 900. The radiopaque anchor 900 is configured to be implanted in the nadir (hinge point) of the non-coronary, right coronary, and/or left-coronary cusps to serve as markers for identification of the proper plane for valve deployment. However, the radiopaque anchor 900 may be used in other anatomical locations for different procedures, as desired. The radiopaque anchor 900 may have dimensions in the range of about 0.5 millimeters (mm) to about 2.0 mm, about 0.75 mm to about 1.75 mm, or about 1.0 to about 1.5 mm. In some cases, the radiopaque anchor 900 may have dimensions of less than 0.5 mm or greater than 2.0 mm, as desired. It is contemplated that the size of the radiopaque anchor 900 may be determined based on the anatomical location it will be implanted.

The radiopaque anchor 900 includes a generally helical body 906 extending from a proximal end region 902 to a distal end region 904. The distal end region 904 may include a pointed distal end 908, although this is not required. It is contemplated that the radiopaque anchor 900 may be deployed into the target region such that it is "screwed" into the tissue. For example, the radiopaque anchor 900 may be rotated as it exits the lumen of the delivery catheter to secure the radiopaque anchor 900 within the tissue. When so provided, a pointed distal end 908 may puncture the tissue to facilitate distal advancement of the radiopaque anchor within the tissue.

The radiopaque anchor 900 may be formed from a shape memory or superelastic material, such as, but not limited to, nitinol. However, this is not required. The radiopaque anchor 900 may be coated with, doped with, alloyed with, or otherwise include radiopaque materials, such as, but not limited to, iodine, barium sulfate, iridium, platinum, tantalum, gold, palladium, tungsten, tin, silver, titanium, nickel, zirconium, rhenium, bismuth, molybdenum, combinations thereof, and the like). These are just some examples of how the radiopaque anchor 900 may be made radiopaque. Other materials and/or techniques may be used as desired.

The radiopaque anchor 900 may be formed such that the body 906 forms a helix when the radiopaque anchor 900 is in the "remembered" or preformed shape. A biasing force (such as a deployment tube) may bias the body 906 such that it has a reduced profile relative to the preformed or deployed shape. For example, the biasing force may reduce the diameter of the helical body 906 while increasing a length thereof. Once the biasing force is removed the helical body 906 returns to its expanded configuration. However, in some cases, the radiopaque anchor 900 may be delivered to the deployment location in the expanded configuration.

The radiopaque anchors 300, 400, 450, 500, 550, 600, 650, 700, 750, 900 may be delivered using similar methods. The radiopaque anchor 300, 400, 450, 500, 550, 600, 650, 700, 750, 900 may be loaded into a delivery device using known techniques. To deploy the radiopaque anchor 300, 400, 450, 500, 550, 600, 650, 700, 750, 900 within the body, the delivery device may be advanced through an outer sheath introduced into the right femoral artery, although other access points may be used as desired. The delivery device may be advanced through the outer sheath to the desired treatment location. In the case of a TAVR procedure, the delivery device may be advanced into the ascending aorta or adjacent to the aortic valve. Once the delivery device is in position, a radiopaque fluid and/or contrast agent may be delivered to the anatomy adjacent to the distal end region through a lumen of the delivery device. The radiopaque fluid and/or contrast agent may be used to identify the cusps of valve and one or more implant locations for at least one radiopaque anchor 300, 400, 450, 500, 550, 600, 650, 700, 750. The delivery device may then be oriented such that a distal opening of a delivery lumen is aligned with the desired implant location. The radiopaque anchor 300, 400, 450, 500, 550, 600, 650, 700, 750, 900 may be loaded into the delivery lumen of the delivery system using known techniques Once the delivery device is in position a guidewire or other penetrating member may be advanced from the distal end of the delivery device so that it penetrates the target tissue (e.g., the left coronary cusp, right coronary cusp, and/or non-coronary cusp in the case of TAVR) to form a hole or channel. In some cases, the radiopaque anchor 300, 400, 450, 500, 550, 600, 650, 700, 750, 900 may be deployed directly into the tissue without the formation of a hole or channel. After formation of the hole or channel, the guidewire may be removed from the delivery device. However, in some cases, such as, but not limited to, when the radiopaque anchor 300, 400, 450, 500, 550, 600, 650, 700, 750, 900 includes a lumen extending therethough, the guidewire may be left in the delivery device and/or in the tissue during deployment of the radiopaque anchor 300, 400, 450, 500, 550, 600, 650, 700, 750.

A push member may then be used to distally advance the radiopaque anchor 300, 400, 450, 500, 550, 600, 650, 700, 750, 900 into the tissue. The radiopaque anchor 300, 400, 450, 500, 550, 600, 650, 700, 750, 900 may include features, such as barbs, hooks, enlarged end regions, etc. that preclude or limits dislodgement (e.g., proximal movement) of the radiopaque anchor 300, 400, 450, 500, 550, 600, 650, 700, 750. Once the radiopaque anchor 300, 400, 450, 500, 550, 600, 650, 700, 750, 900 is anchored within the tissue, the push member and/or delivery device can be proximally retracted. In some cases, the guidewire, push member and/or delivery device may be fully removed from body. In other cases, the guidewire, push member and/or delivery device may be proximally retracted but remain in the body (e.g., displaced from the area of valve implantation).

In some cases, the radiopaque anchor 300, 400, 450, 500, 550, 600, 650, 700, 750, 900 may be implanted within the tissue such that the proximal end thereof is fully within the tissue. In other embodiments, the radiopaque anchor 300, 400, 450, 500, 550, 600, 650, 700, 750, 900 may be implanted within the tissue such that the proximal end thereof is flush with or about at the surface of the tissue. In yet other embodiments, the radiopaque anchor 300, 400, 450, 500, 550, 600, 650, 700, 750, 900 may be implanted within the tissue such that the proximal end thereof extends from the surface of the tissue. Once the radiopaque anchor 300, 400, 450, 500, 550, 600, 650, 700, 750, 900 has been delivered, the delivery device may be used to deliver one or more additional radiopaque anchors 300, 400, 450, 500, 550, 600, 650, 700, 750, 900 to one or more additionally locations. For example, one or more radiopaque anchors 300, 400, 450, 500, 550, 600, 650, 700, 750, 900 may be delivered to each cusp to improve visualization of the anatomy under fluoroscopy. In other cases, a radiopaque anchor 300, 400, 450, 500, 550, 600, 650, 700, 750, 900 may be positioned in each cusp. It is further contemplated that more than one dual lumen pigtail catheter may be used to deploy radiopaque anchors 300, 400, 450, 500, 550, 600, 650, 700, 750, 900 in each cusp simultaneously or substantially simultaneously.

It is contemplated that the implantation of one or more radiopaque anchors 300, 400, 450, 500, 550, 600, 650, 700, 750, 900 may reduce contrast injections within the patient. For example, once the radiopaque anchors 300, 400, 450, 500, 550, 600, 650, 700, 750, 900 are positioned, the radiopaque anchors 300, 400, 450, 500, 550, 600, 650, 700, 750, 900 are able to provide beacons for positioning of the TAVR valve. Further, as the pigtail catheter is not necessary for contrast injections after implantation of the radiopaque anchors 300, 400, 450, 500, 550, 600, 650, 700, 750, the pigtail catheter (or other delivery system) can be removed from the anatomy which may help facilitate delivery of the TAVR valve (e.g., fewer devices are in the vasculature during delivery of the TAVR valve). Additionally, the radiopaque anchors 300, 400, 450, 500, 550, 600, 650, 700, 750, 900 may enable better visualization of the annulus plane during implantation of the valve while clearly identifying the orientation of the radiopaque anchor 300, 400, 450, 500, 550, 600, 650, 700, 750, 900 relative to the annular plane of the valve.

Additionally, or alternatively, to the implantation of one or more radiopaque anchors, it may be desirable to control the depth of the implant. While transesophageal echocardiography may be used to facilitate visualization, it may be considered invasive and/or lack three-dimensional imaging capabilities. In some cases, aortography may be used; however, this may provide two-dimensional, partial reference-based imaging which relies on the ability of the contrast to fill the base of the native coronary cusps. Contrast aortography of a coaxial projection of the valve prosthesis may not show the representative depth relative to the native annulus. It may be desirable to provide a system and method for better controlling TAVR implant depth.

Figure 19:
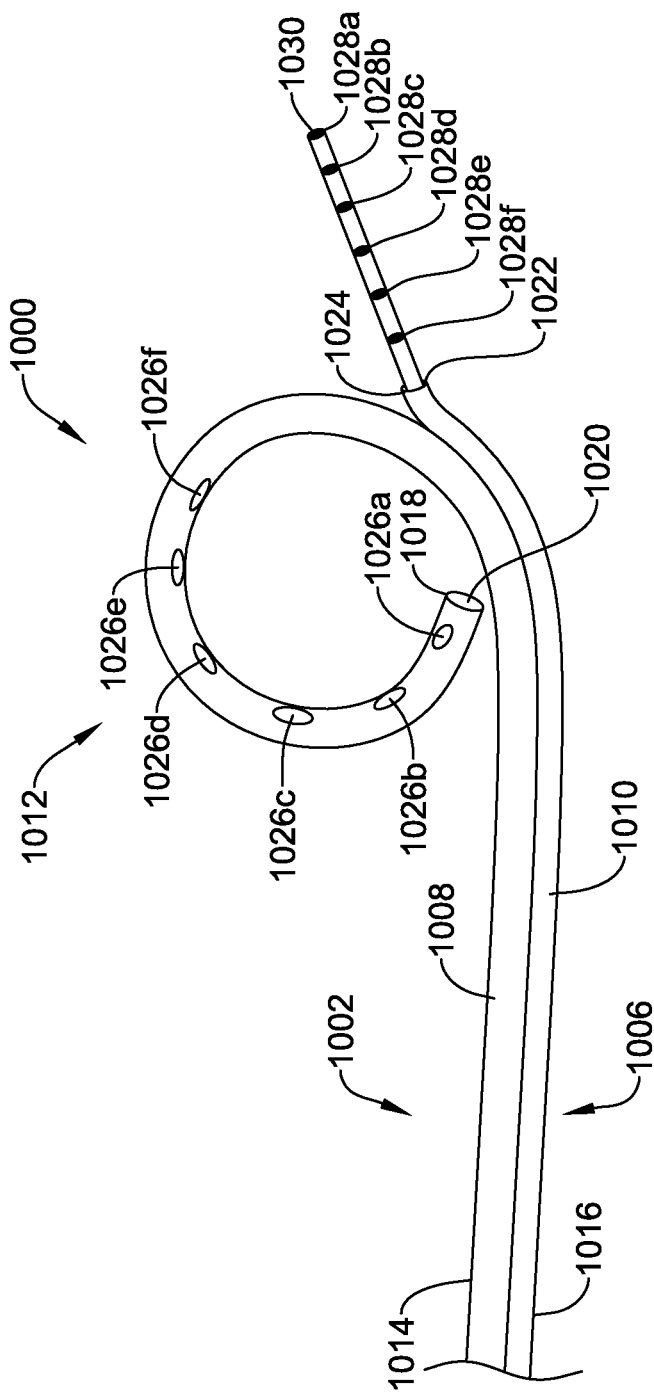
FIG. 19 is a perspective view of an illustrative system for measuring a guiding an implant depth.

FIG. 19 is perspective view of an illustrative system 1000 for measuring and guiding implant depth during a TAVR procedure. Generally, the system 1000 may include a pigtail catheter 1002 and an implant-depth wire 1004. While the system 1000 is described a utilizing a pigtail catheter 1002, other catheters, sheaths, etc. may be used, as desired. The pigtail catheter 1002 may be similar in form and function to the pigtail catheter 204 described herein. It is contemplated that other pigtail catheter 1002 configurations, such as, but not limited to the pigtail catheter 104 described herein, may also be used.

The pigtail catheter 1002 includes a tubular elongate shaft 1006 extending from a proximal end configured to remain outside the body to the distal end region 1012. The elongate shaft 1006 includes at least a first lumen 1008 configured to deliver a radiopaque fluid and/or a contrast fluid and a second lumen 1010 configured to deliver an implantable radiopaque marker. In some cases, the first lumen 1008 may have a diameter in the range of about 3 to about 5 French to allow for contrast injection and/or pressure measure. The second lumen 101 may have a diameter in the range of about 1 to about 3 French to slidably receive the implant-depth wire 1004. The two or more lumens 1008, 1010 may be arranged in a side by side or collinear arrangement, in a coaxial or tube within a tube arrangement, or combinations thereof. The two or more lumens 1008, 1010 may be fluidly isolated from another The elongate shaft 1006 may include a first portion 1014 defining the first lumen 1008 and a second portion 1016 defining the second lumen 1010. It is contemplated that the first and second portions 1014, 1016 need not have the same length as each other. In some embodiments, the elongate shaft 1006 may be extruded as a single monolithic structure to form side-by-side lumens 1008, 1010. In other embodiments, the elongate shaft 1006 may be formed by other suitable means, such as a first and a second separate extruded tubes arranged side-by-side and connected by adhesive, or the like.

The first lumen 1008 may extend from the proximal end of the first portion 1014 towards a distal end 1018 thereof. In some cases, the first lumen 1008 may terminate proximal to the distal end 1018 of the first portion 1014 while in other cases, the first lumen 1008 may extend to the distal end 1018 to define a distal opening 1020. The second lumen 1010 may extend from the proximal end of the second portion 1016 towards a distal end 1024 thereof. The second lumen 1010 may extend to the distal end 1024 to define a distal opening 1022 (e.g., distally facing). However, this is not required. In some cases, the second lumen 1010 may terminate proximal to the distal end 1024. In such an instance, a side port may be provided to allow an implant-depth wire 1004 to be advanced through and exit the second lumen 1010.

In the absence of an external biasing force, or in a deployed configuration, the distal end region 1012 is configured to assume a curved pigtail or J shape. It is contemplated that the distal end region 1012 may have any degree of curvature desired including less than 360° or greater than 360°, as desired. The distal end region 1012 may be biased into a generally linear, or delivery, configuration by, for example, a guidewire or stiffening member slidably disposed within the lumen 1008 or a stiffer tube (such as, but not limited to an outer sheath) disposed over an outer surface of the pigtail catheter 1002. These are just examples and are not intended to limit the pigtail catheter 1002 to a particular configuration.

The first portion 1014 includes a set of holes or apertures 1026a, 1026b, 1026c, 1026d, 1026e, 1026f (collectively, 1026). The set of apertures 1026 may include one, two, three, four, or more apertures, as desired. The set of apertures 1026 may be in fluid communication with a radiopaque fluid source and/or a contrast fluid source. As described herein, the second portion 1016 may include a distal opening 1022 through which an implant-depth wire 1004 is deployable. For example, the implant-depth wire 1004 may be pushed out of the distal opening 1022 and into the nadir of a cusp of the aortic valve, as will be described in more detail herein. In some cases, the distal end 1024 of the second portion 1016 may extend slightly around the curve of the pigtail portion such that the distal opening 1022 is configured to direct the implant-depth wire 1004 orthogonal to the tissue at the center of the cusp, although this is not required.

In some cases, the set of apertures 1026 may be positioned on the first portion 1014 such that when the distal end region 1012 of the pigtail catheter 1002 is in the deployed configuration, the set of apertures 1026 are positioned or directed radially inwards relative to the curve of the distal end region 1012 (or on the concave surface thereof). However, this is not required. In some cases, the first set of apertures 1026 may be positioned on the elongate shaft 1006 such that when the distal end region 1012 of the pigtail catheter 1002 is in the deployed configuration the first set of apertures 1026 are positioned or directed radially outwards (not explicitly shown) relative to the curve of the distal end region 1012 (or on the convex surface thereof). It is contemplated that the position of the set of apertures 1026 is not limited to the radially inward or outward surface of the distal end region 1012. It is contemplated that the set of apertures 1026 may be positioned at any circumferential location about the portion 1014, or combinations of circumferential locations, as desired.

The implant-depth wire 1004 may be an elongate wire or other elongate structure having a cross-section sized to slide within the second lumen 1010 of the pigtail catheter 1004. In some cases, the implant-depth wire 1004 may have a generally solid cross-section while in other cases, the implant-depth wire 1004 may be generally tubular. The implant-depth wire 1004 may include a plurality of radiopaque markers 1028a, 1028b, 1028c, 1028d, 1028e, 1028f (collectively, 1028) spaced along a length thereof. In some cases, a first radiopaque marker 1028a may be positioned at a distal end 1030 of the implant-depth wire 1004. The implant-depth wire 1004 may include any number of radiopaque markers 1028 desired, such as, but not limited to, one, two, three, four, five, six, or more. The radiopaque markers 1028 may be evenly or uniformly spaced along a distal end region of the implant-depth wire 1004. For example, the radiopaque markers 1028 may be spaced in the range of 1 to 10 millimeters, in the range of 2 to 8 millimeters, or about 5 millimeters from one another. In some cases, the radiopaque markers 1028 may extend proximally along at least a portion of a length of the implant-depth wire 1004 such that the radiopaque markers 1028 may be used to help verify coronary artery heights during the procedure. It is contemplated that radiopaque markers 1032a, 1032b, 1032c, 1032d may also be provided on the pigtail catheter 1002 which may be used to help verify coronary artery heights during the procedure. The radiopaque markers 1032 may be similar in form and function to the radiopaque markers 1028.

Radiopaque materials are understood to be materials capable of producing a relatively bright image on a fluoroscopy screen or another imaging technique during a medical procedure. This relatively bright image aids the user of the system 1000 in determining its location. Some examples of radiopaque materials can include, but are not limited to, gold, platinum, palladium, tantalum, tungsten alloy, polymer material loaded with a radiopaque filler, and the like.

The radiopaque markers 1028 may be incorporated in the implant-depth wire 1004 in a number of different manners. For example, the material of the implant-depth wire 1004 may be doped with a radiopaque material at predefined intervals to provide radiopaque regions. In other cases, radiopaque material may be embedded into a thickness of the implant-depth wire 1004. In yet another example, radiopaque cuffs may be positioned over an outer surface of the implant-depth wire 1004 and attached thereto. It is further contemplated that the entire implant-depth wire 1004 may be formed from a radiopaque material. In such an instance, material may be removed from the implant-depth wire 1004 to form regions having a reduced cross-sectional dimension at predefined intervals. The region having the smaller cross-sectional dimension may function as the distance identifiers.

It is contemplated that the implant-depth wire 1004 may be provided with features configured to facilitate advancement of the implant-depth wire 1004 into bodily tissue. In some cases, the distal end 1030 of the implant-depth wire 1004 may be pointed or include a needle-tip to penetrate the tissue. In one example, the implant-depth wire 1004 may include a telescoping needle such that the needle can retract once the tissue has been penetrated. Alternatively, or additionally, the distal end 1030 of the implant-depth wire 1004 may include an electrode such that radiofrequency (RF) energy may be delivered to facilitate penetration of the tissue. In such an instance, a length of the implant-depth wire 1004 may be insulated so as the limit the RF energy delivery to the distal end 1030.

Figure 20:
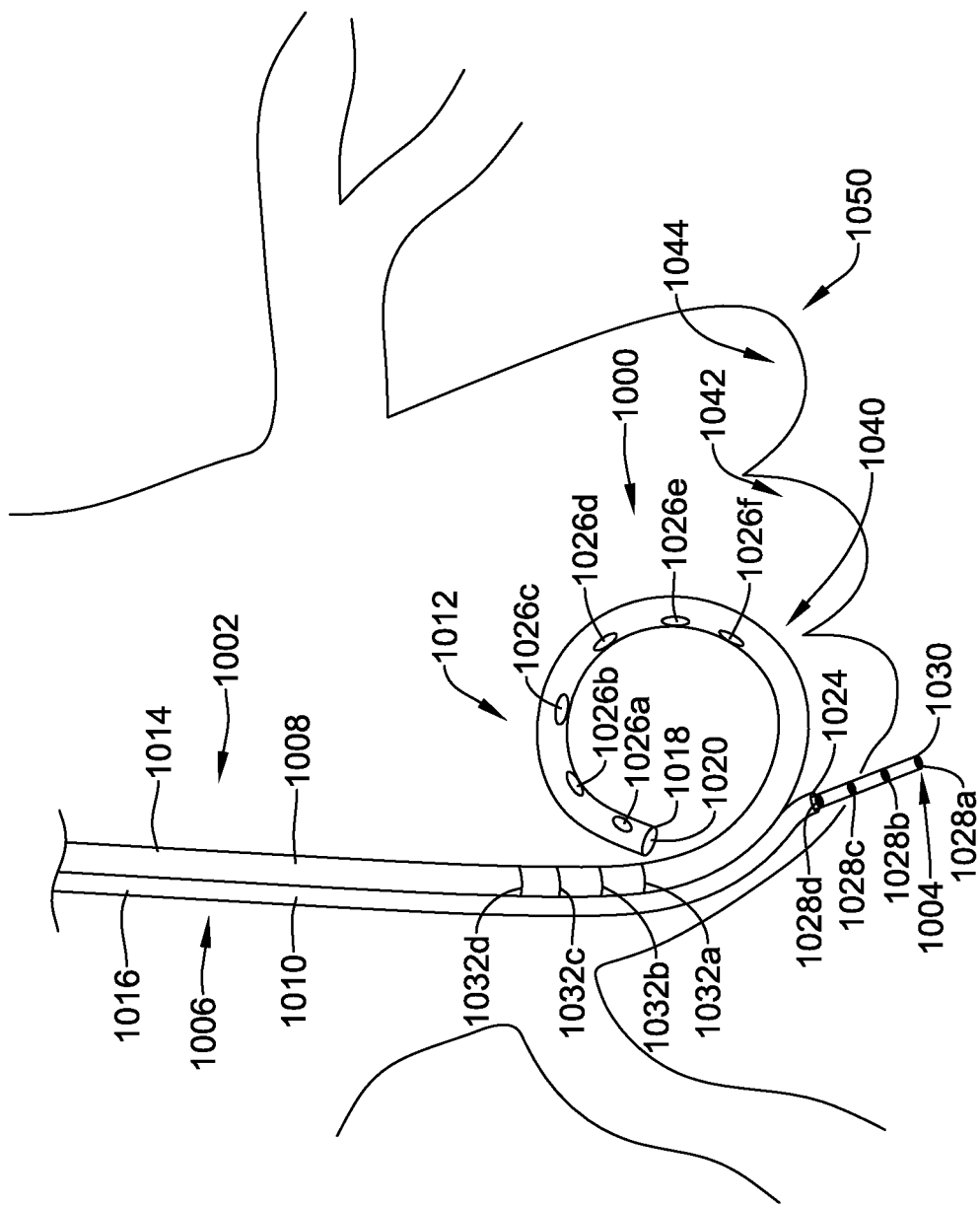
FIG. 20 is a schematic view of the illustrative system of FIG. 19 in situ.

Referring now to FIG. 20, which illustrates the system 1000 for measuring and guiding implant depth during a TAVR procedure in use, the pigtail catheter 1002 is first positioned in the non-coronary cusp (NCC) 1040 of the aortic valve 1050. In other cases, the pigtail catheter 1002 may be positioned in the right coronary cusp (RCC) 1042 or the left coronary cusp (LCC) 1044. The implant-depth wire 1004 may then be distally advanced from the distal opening 1022 of the second portion 1016 of the pigtail catheter 1002. The implant-depth wire 1004 may penetrate the nadir of the NCC 1040. The distal end region 1012 of the pigtail catheter 1002 and/or the distal end region of the implant-depth wire 1004 may include retention features, such as, but not limited to barbs, spikes, etc. configured to temporarily secure the system 1000 to the body tissue. The implant (e.g., TAVR valve) may then be delivered using the radiopaque markers 1028 as a guide. The implant-depth wire 1004 may provide a simple and intuitive system to help guide the depth of the implant of any valve system without requiring a change to clinical workflow of a valve replacement procedure. Once the implant is positioned and deployed, the implant-depth wire 1004 and the pigtail catheter 1002 may be removed.

To facilitate delivery of the pigtail catheter 1002 and/or the implant-depth wire 1004, a proximal end region of the system 1000 may be provided with a locking mechanism to secure the implant-depth wire 1004 relative to the pigtail catheter. For example, the locking mechanism may secure the implant-depth wire 1004 relative to the pigtail catheter 1002 such that the implant-depth wire 1004 remains within the second lumen 1010 during advancement of the pigtail catheter 1002 while the system 1000 is being advanced through the vasculature. It is further contemplated that the locking mechanism may be used to secure the implant-depth wire 1004 relative to the pigtail catheter 1002 after the implant-depth wire 1004 has been advanced into the body tissue. Some illustrative locking mechanisms may include, but are not limited to, friction fits, tongue and groove fits, or other mechanical interfaces, as desired. Some illustrative locking mechanisms are described in commonly assigned U.S. patent application Ser. No. 17/031,070, titled WEDGE-LOCK SHEATH RETENTION MECHANISM, Ser. No. 16,811,296, titled, PINCH-LOCK SHEATH RETENTION MECHANISM, and Ser. No. 16/280,104, titled MEDICAL DEVICE RELEASE SYSTEM, the disclosures of which are hereby incorporated by reference.

Figure 21:
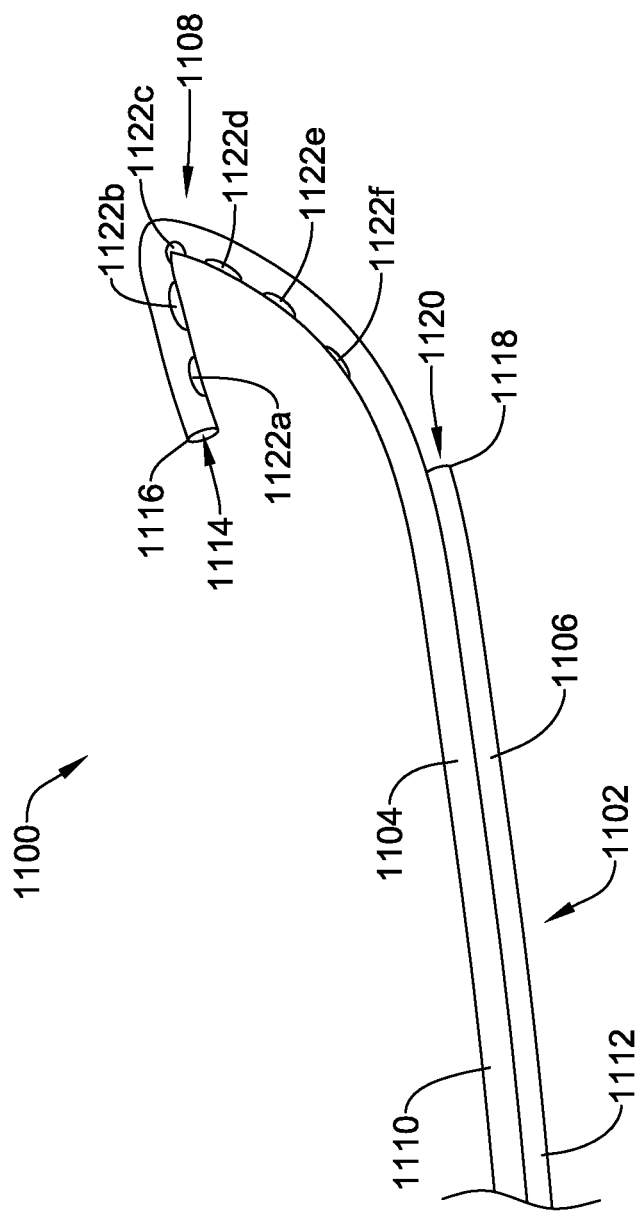
FIG. 21 is a side view of another illustrative pigtail catheter.

FIG. 21 is side view of an illustrative pigtail catheter 1100 for deploying an implant-depth wire 1004 or delivering a radiopaque implant such as those described herein. The pigtail catheter 1100 includes a tubular elongate shaft 1102 extending from a proximal end configured to remain outside the body to the distal end region 1108. The elongate shaft 1102 includes at least a first lumen 1104 configured to deliver a radiopaque fluid and/or a contrast fluid and a second lumen 1106 configured to deliver an implantable radiopaque marker. In some cases, the first lumen 1104 may have a diameter in the range of about 3 to about 5 French to allow for contrast injection and/or pressure measure. The second lumen 101 may have a diameter in the range of about 1 to about 3 French to slidably receive the implant-depth wire 1004 (or radiopaque implant). The two or more lumens 1104, 1106 may be arranged in a side by side or collinear arrangement, in a coaxial or tube within a tube arrangement, or combinations thereof. The two or more lumens 1104, 1106 may be fluidly isolated from another The elongate shaft 1102 may include a first portion 1110 defining the first lumen 1104 and a second portion 1112 defining the second lumen 1106. It is contemplated that the first and second portions 1110, 1112 need not have the same length as each other. In some embodiments, the elongate shaft 1102 may be extruded as a single monolithic structure to form side-by-side lumens 1104, 1106. In other embodiments, the elongate shaft 1102 may be formed by other suitable means, such as a first and a second separate extruded tubes arranged side-by-side and connected by adhesive, or the like.

The first lumen 1104 may extend from the proximal end of the first portion 1110 towards a distal end 1116 thereof. In some cases, the first lumen 1104 may terminate proximal to the distal end 1116 of the first portion 1110 while in other cases, the first lumen 1104 may extend to the distal end 1116 to define a distal opening 1114. The second lumen 1106 may extend from the proximal end of the second portion 1112 towards a distal end 1118 thereof. The second lumen 1106 may extend to the distal end 1118 to define a distal opening 1120 (e.g., distally facing). However, this is not required. In some cases, the second lumen 1106 may terminate proximal to the distal end 1118. In such an instance, a side port may be provided to allow an implant-depth wire 1004 to be advanced through and exit the second lumen 1106.

In the absence of an external biasing force, or in a deployed configuration, the distal end region 1108 is configured to assume a curved pigtail or J shape. It is contemplated that the distal end region 1108 may have any degree of curvature desired including less than 360° or greater than 360°, as desired. For example, the distal end region 1108 may be custom-formed to an individual patient's anatomy based on pre-operative imaging. Alternatively, the clinician may select from a variety of catheter shapes to fit (as closely as possible) the patient's non-coronary cusp anatomy. The pigtail catheter 1100 illustrated in FIG. 21 is just one illustrative example of how the curved distal end region 1108 may vary for a patient's anatomy. The distal end region 1108 may be biased into a generally linear, or delivery, configuration by, for example, a guidewire or stiffening member slidably disposed within the lumen 1104 or a stiffer tube (such as, but not limited to an outer sheath) disposed over an outer surface of the pigtail catheter 1100. These are just examples and are not intended to limit the pigtail catheter 1100 to a particular configuration.

The first portion 1110 includes a set of holes or apertures 1122a, 1122b, 1122c, 1122d, 1122e (collectively, 1122). The set of apertures 1122 may include one, two, three, four, or more apertures, as desired. The set of apertures 1122 may be in fluid communication with a radiopaque fluid source and/or a contrast fluid source. As described herein, the second portion 1112 may include a distal opening 1120 through which an implant-depth wire 1004 is deployable. For example, the implant-depth wire 1004 may be pushed out of the distal opening 1120 and into the nadir of a cusp of the aortic valve, as will be described in more detail herein. In some cases, the distal end 1118 of the second portion 1112 may extend slightly around the curve of the pigtail portion such that the distal opening 1120 is configured to direct the implant-depth wire 1004 orthogonal to the tissue at the center of the cusp, although this is not required.

In some cases, the set of apertures 1122 may be positioned on the first portion 1110 such that when the distal end region 1108 of the pigtail catheter 1100 is in the deployed configuration, the set of apertures 1122 are positioned or directed radially inwards relative to the curve of the distal end region 1108 (or on the concave surface thereof). However, this is not required. In some cases, the first set of apertures 1122 may be positioned on the elongate shaft 1102 such that when the distal end region 1108 of the pigtail catheter 1100 is in the deployed configuration the first set of apertures 1122 are positioned or directed radially outwards (not explicitly shown) relative to the curve of the distal end region 1108 (or on the convex surface thereof). It is contemplated that the position of the set of apertures 1122 is not limited to the radially inward or outward surface of the distal end region 1108. It is contemplated that the set of apertures 1122 may be positioned at any circumferential location about the portion 1110, or combinations of circumferential locations, as desired.

As used herein, the relative terms "proximal" and "distal" shall be defined from the perspective of the delivery system. Thus, proximal refers to the direction of the handle portion of the delivery system and distal refers to the direction of the distal tip.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Although certain embodiments and examples have been described herein, it may be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art may recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. The ranges disclosed herein also encompass any and all overlap, subranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm." Phrases preceded by a term such as "substantially" include the recited phrase and should be interpreted based on the circumstances (e.g., as much as reasonably possible under the circumstances). For to example, "substantially straight" includes "straight."

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A system, comprising:
   a pigtail catheter, the pigtail catheter comprising:
   an elongate shaft extending from a proximal end to a distal end, the elongate shaft defining:
   a first lumen extending distally from a proximal end, the first lumen in fluid communication with one or more apertures extending through a side wall of the elongate shaft; and
   a second lumen extending distally from a proximal end, the second lumen in fluid communication with at least one opening in the elongate shaft, wherein the at least one opening in the elongate shaft is distally facing; and
   an implantable radiopaque anchor configured to be permanently implanted within tissue, the implantable radiopaque anchor slidably disposed within the second lumen of the elongate shaft, wherein the implantable radiopaque anchor includes a single linear tubular body having a distal end region and a proximal end region and a plurality of barbs extending radially outward and proximally from the distal end region, such that the plurality of barbs precludes dislodgement of the implantable radiopaque anchor proximally from the tissue.

2. The system of claim 1, wherein the at least one opening in the elongate shaft extends through the side wall of the elongate shaft.

3. The system of claim 1, wherein the proximal end region of the implantable radiopaque anchor comprises a plurality of barbs, wherein the plurality of barbs of both the distal end region and the proximal end region includes one or more tines.

4. The system of claim 3, wherein the one or more curved tines in the proximal end region are movable between an expanded deployed configuration and a compressed delivery configuration.

5. The system of claim 1, wherein the implantable radiopaque anchor comprises a biodegradable polymer doped with or carrying a radiopaque material.

6. The system of claim 1, wherein the implantable radiopaque anchor is at least partially formed from a shape memory material.

7. A system for guiding implant depth, the system comprising:
   a pigtail catheter, the pigtail catheter comprising:
   an elongate shaft extending from a proximal end to a distal end, the elongate shaft defining:
   a first lumen extending distally from a proximal end to the distal end of the elongate shaft, the first lumen in fluid communication with one or more apertures extending through a side wall of the elongate shaft, wherein the one or more apertures are disposed along a distal region of the pigtail catheter configured to form a curving region when deployed;

and a second lumen extending distally from a proximal end to a distal end positioned proximal of the one or more apertures extending through the side wall of the elongate shaft, the distal end of the second lumen defining a distally facing opening;

wherein the first lumen and the second lumen are disposed side-by-side;

and implantable radiopaque anchor configured to be permanently implanted within tissue, the implantable radiopaque anchor slidably disposed within the second lumen of the elongate shaft.

8. A method for deploying an implantable radiopaque anchor, the method comprising:

advancing the pigtail catheter of claim 1 through the vasculature to a target location;

identifying an implant location;

advancing a penetrating member through the pigtail catheter to form a channel in a tissue at the implant location and then removing the penetrating member from the pigtail catheter; and inserting an implantable radiopaque anchor within the channel, wherein the implantable radiopaque anchor includes a tubular body and a plurality of barbs extending radially outward and proximally from only a distal end region of the tubular body, such that the plurality of barbs precludes dislodgement of the implantable radiopaque anchor proximally from the tissue.

9. The method of claim 8, wherein identifying the implant location includes administering a radiopaque fluid or contrast agent adjacent to the target location.

10. The method of claim 8, wherein inserting the implantable radiopaque anchor within the channel comprises actuating the implantable radiopaque anchor through the second lumen of the pigtail catheter and out the at least one distally facing opening in the side wall of the pigtail catheter.

11. The system of claim 1, wherein the implantable radiopaque anchor has a lumen extending longitudinally through the single linear tubular body.

12. The method of claim 10, wherein the implantable radiopaque anchor has a lumen extending longitudinally through the tubular body, and wherein distally actuating the implantable radiopaque anchor through the second lumen of the pigtail catheter includes sliding the implantable radiopaque anchor over a guidewire disposed within the second lumen.

* * * * *